United States Patent [19]

Karen et al.

[11] Patent Number: 5,168,457

[45] Date of Patent: Dec. 1, 1992

[54] APPARATUS FOR IDENTIFYING AND COMPARING LATTICE STRUCTURES AND DETERMINING LATTICE STRUCTURE SYMMETRIES

[75] Inventors: Vicky L. Karen, Highland; Alan D. Mighell, Rockville, both of Md.

[73] Assignee: The United States of America as represented by the Secretary of Commerce, Washington, D.C.

[21] Appl. No.: 434,383

[22] Filed: Nov. 13, 1989

[51] Int. Cl.⁵ ............................................. G01N 33/00
[52] U.S. Cl. ................................... 364/497; 505/842
[58] Field of Search .............................. 364/497–499; 505/842, 843

[56] References Cited

U.S. PATENT DOCUMENTS 4,855,931  8/1989  Saunders ............................... 364/499
4,897,796  1/1990  Salvado ................................. 364/497

Primary Examiner—Joseph L. Dixon
Attorney, Agent, or Firm—Kirk M. Hudson

[57] ABSTRACT

A converse transformation matrix generation approach is used either i) to relate a lattice structure of one crystalline material to the lattice structure(s) of one or more other crystalline materials for determining interlattice relationships which allow materials to be identified and classified relative to other materials; or ii) to relate a lattice structure of a material to itself for determining lattice symmetry. In particular, matrices which transform any primitive cell defining a lattice structure either into itself or into another cell defining a second lattice structure to within predetermined maximum tolerances of the cell parameters are generated.

37 Claims, 14 Drawing Sheets

Fig. 10

952 Use symmetry matrices Hs to generate equivalent (h, k, l)'s

954 If necessary, calculate absorption corrections from morphology data derived in step 940 and apply to equivalent (h, k, l)'s

956 Establish the Laue symmetry

958 Calculate the nature and directions of the symmetry axes

959 Use the symmetry axis data from step 958 to obtain sample orientations for photographs of symmetry

Fig. 11

962 Calculate an idealized cell using the cell parameter errors determined in step 930

964 Reduce the idealized cell

966 Search the International Tables for Crystallography for a transformation matrix to transform the reduced idealized cell of step 964 to a conventional cell

APPARATUS FOR IDENTIFYING AND COMPARING LATTICE STRUCTURES AND DETERMINING LATTICE STRUCTURE SYMMETRIES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND AND SUMMARY

This invention relates generally to apparatus and methods for identifying lattice structures, and more particularly to apparatus and methods for identifying intralattice and interlattice relationships.

A knowledge of the nature of the lattice structure of a material, as well as how it relates to the lattice structures of other materials, is essential in any systematic analysis of physical properties, and has many important commercial applications. For example, in crystallography, it is important for further analysis and identification of a crystalline structure under investigation to determine its symmetry characteristics. As another example, in materials design, once a new compound has been synthesized with a sought-after property, it can be extremely useful to the researcher to find all other materials that bear some specified lattice relationship. Thus, for example, once related compounds have been identified which bear a given lattice relationship to a new superconducting material, the related compounds can then be evaluated to see if they also exhibit superconductivity.

As still other examples, it can be important for the researcher to know whether two apparently different materials exhibiting the same property have the same or a derivative lattice relationship, or to identify an unknown phase by matching the unknown against all known lattice structures. Additionally, the researcher may wish to analyze structural lattice relationships within a large set of compounds, or between two sets of compounds.

Heretofore, analysis of lattice structures, both to determine intralattice relationships (e.g., lattice symmetries) and to determine interlattice relationships, has been difficult, cumbersome and subject to substantial error. For example, in the collection of crystallographic data, the experimentalist traditionally has relied on familiar or standard orientations to guide both the initial collection of data and evaluation thereof to define the lattice and the crystal symmetries. On a diffractometer, for example, a conventional unit cell, as defined by the magnitudes of the cell parameters, is determined and the assumed Laue symmetry is verified by taking specially oriented films or by checking the intensities of equivalent (h,k,l)'s listed for standard orientations. While there are many valid reasons for choosing conventional cells and orientations in the latter stages of experimental work, by choosing specific or familiar orientations in the initial stages, assumptions are made which influence what data are collected, and consequently, mistakes are more likely to be made.

In accordance with the present invention, a converse transformation matrix generation approach is used either i) to relate a lattice structure of one material to the lattice structure(s) of one or more other materials for determining interlattice relationships which allow materials to be identified and classified relative to other materials; or ii) to relate a lattice structure of a material to itself for determining lattice symmetry. The matrix approach is an extremely powerful, efficient and flexible analytical tool which is readily implemented and avoids the constraints and error inherent in the conventional approaches heretofore used. For example, the matrix approach is substantially more effective than prior approaches because it will maintain its selectivity in matching lattice structures despite the rather large experimental errors that are routinely associated with electron diffraction data. As another example, the determination of lattice symmetry using the matrix approach of the present invention does not require that the lattice and its symmetry be expressed with respect to a standard cell or a standard orientation. The properties of the lattice are reflected in any primitive cell because translation of the primitive unit cell generates the entire lattice. In accordance with the present invention, the symmetry matrices which transform the lattice into itself are generated, and are used to determine the metric symmetry and any pseudosymmetry, as well as the Laue symmetry, group-subgroup relationships, the nature and directions of symmetry axes, and conventional or standard cells. In addition, the determination of standard or conventional cells is greatly simplified. In contrast to other methods for determining standard cells, the matrix approach of the present invention permits working with symmetry directly in the form of matrices, and not with the magnitude of lattice parameters and their associated errors. Calculations are straightforward and a transformation matrix is found using linear algebra techniques.

Still further, the matrix approach of the present invention enables computer-based controllers for commercial diffractometers (x-ray, neutron and electron) to be implemented which fully automate the diffractometry process in a theoretically and experimentally correct and error-free manner. Unlike procedures currently used in diffractometry, errors in strategy are impossible with the matrix approach because at each step exactly the right data for control decisions are directly available in a clear, logical and concise format. Since the matrix approach is extremely reliable, its use will prevent errors in symmetry and structure determinations, which is widely recognized as a very serious current problem resulting in erroneous symmetry determinations in about five percent of the approximately 25,000 full structure determinations carried out annually.

The matrix approach of the present invention also enables electron diffractometry to be converted from a two dimensional technique that focuses primarily on d-spacings to a three dimensional technique similar to that employed in single crystal x-ray and neutron diffractometry. The ability to determine the cell structure and symmetry from data collected on extremely small samples and to identify the structure using computerized databases of known structures represents a new and comprehensive method to identify crystalline phases.

The matrix approach of the present invention thus represents a powerful new strategy for lattice structure analysis in which the emphasis is shifted from standard cells and standard orientations to matrices.

A portion of the present invention's matrix approach to lattice analysis in the context of determining symmetry has been discussed in detail by the present applicants in their article "A Matrix Approach to Symmetry", *Acta Cryst.* (1987) A43, pp. 375–384, which is hereby incorporated by reference. However, no method for generating the necessary symmetry matrices which relate any observed primitive cell of a lattice to itself is described in the aforesaid article, or in any other published article. The general converse transformation method described herein which applicants have developed generates matrices relating any two lattice cells (including a lattice cell to itself); and can be used in new, more efficacious methods for control of diffractometers, and for phase identification using analytical electron microscope (AEM) data and existing large scale databases providing chemical, physical and crystallographic data on solid-state materials.

Accordingly, it is a primary object of the present invention to provide apparatus and methods for identifying lattice structures using the converse transformation matrix generation method of the present invention.

It is a further primary object of the present invention to provide apparatus and methods for identifying unknown materials using electron diffraction and energy dispersive spectroscopy data, available databases on solid-state materials and the converse transformation matrix generation method of the present invention.

It is a still further primary object of the present invention to provide improved diffractometry apparatus and methods using the converse transformation matrix generation method of the present invention.

In accordance with the present invention, a method of comparing two crystalline materials to determine whether they have a predetermined lattice structure relationship therebetween comprises the steps of:

a) determining primitive lattice cells Y and Z, respectively, for the two materials, the cells Y and Z having three cell edges YA, YB, YC and ZA, ZB and ZC, respectively, and three cell angles YAL, YBE, YGA and ZAL, ZBE and ZGA, respectively;

b) generating all matrices H, if any, which transform cell Z into cell Y within predetermined maximum cell edge an angle tolerances TOLI1, TOLI2, TOLI3, and TOLI4, TOLI5, TOLI6, respectively; and if at least one matrix H is generated;

c) analyzing the nature of the generated matrix (matrices) H and its inverse (their respective inverses) H' to determine the nature of the lattice relationship:

1) If a matrix H has integer matrix elements and a determinant HDET=1, then Cell Z and Cell Y define the same lattice;

2) If a matrix H or its inverse H' has integer matrix elements and a determinant HDET greater than one, then Cell Z and Cell Y are in a subcell/supercell relationship; or 3) If a matrix H and its inverse H' both have one or more fractional matrix elements, then Cell Z and Cell Y define lattices that are in a composite relationship.

In accordance with a further aspect of the present invention, a method for analyzing the symmetry of a crystalline material comprises the steps of:

a) collecting edge data ZA, ZB and ZC and angle data ZAL, ZBE and ZGA defining any primitive lattice cell Z of the material;

b) generating all symmetry matrices Hs which transform cell Z into itself within predetermined maximum cell edge and angle parameter tolerances TOLI1, TOLI2, TOLI3 and TOLI4, TOLI5, TOLI6, respectively;

c) determining the metric symmetry using symmetry matrices Hs; and d) defining the crystal symmetry using symmetry matrices Hs.

In accordance with a still further aspect of the present invention, a method for identifying an unknown crystalline material comprises the steps of;

a) determining a primitive lattice cell Z of the unknown material, the cell Z having three cell edges ZA, ZB, and ZC, respectively, and three cell angles ZAL, ZBE, and ZGA, respectively;

b) determining the chemical composition of the unknown material;

c) searching a database comprising lattice cell data and element type data for materials with known lattice structures and chemical compositions by at least in part generating matrices H identifying all compounds having lattice cell structures related to cell Z;

d) analyzing the matrices H to identify which of the compounds identified in step c) match cell Z by having a lattice cell structure identical to or in a subcell/supercell derivative relationship to cell Z, and saving the lattice cell matching compounds as a first data set;

e) searching the database for all compounds which match the unknown material by having the same element types as the unknown material, and saving the element type matching compounds as a second data set; and f) combining the first and second data sets to derive all known compounds having the same lattice cell structure and element types.

In accordance with another aspect of the present invention, in each of the foregoing methods, the matrices H are generated by a converse transformation method comprising the steps of:

finding all matrix triples AU, AV, AW; BU, BV, BW; CU, CV, CW which accomplish transformation of the respective Z-cell edges to the corresponding edges of the desired cell within the corresponding ones of the maximum cell edge tolerances; and finding all combinations of the matrix triples found in the matrix-triple-finding step which accomplish transformation of the respective Z-cell angles to the corresponding angles of the desired cell within the corresponding ones of the maximum acceptable cell angle tolerances.

These and other objects, features and advantages of the present invention will be described in or apparent from the following detailed description of preferred embodiments.

BRIEF DESCRIPTION OF THE DRAWING

The preferred embodiments will be described with reference to the drawing, in which:

FIG. 10 is a more detailed flow chart of a preferred embodiment of step 950 in FIG. 9.

FIG. 11 is a more detailed flow chart of a first embodiment of step 960 in FIG. 9.

DETAILED DESCRIPTION OF THE PREFERRED EMBODIMENTS

Figure 1:
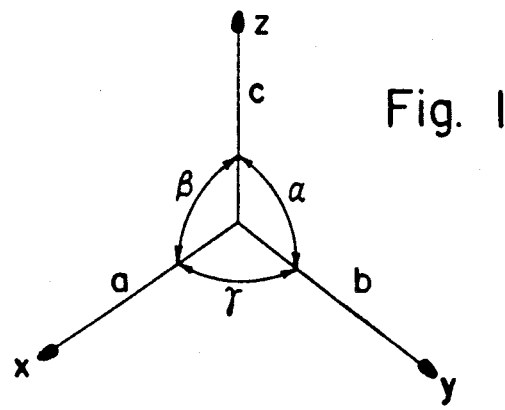
FIG. 1 is a graphical representation of the parameters of a primitive cell of a lattice structure.

Referring to FIG. 1, a primitive or conventional unit cell of a lattice structure, which cell reflects all of the properties of the lattice structure, is defined by six parameters, namely three cell edges a, b and c, and three cell angles $\alpha$, $\beta$ and $\gamma$, as shown. In accordance with the present invention, the relationship between any two lattice structures, and the symmetry characteristics of a single lattice structure, can be determined by calculating in the following manner all $3 \times 3$ transformation matrices H (if any) which have elements that are integers or simple rational numbers, and which relate the two lattice cell structures (or the lattice structure to itself) to within specified tolerances of the lattice cell parameters. In other words cell Y=(H-Matrix) Z. The transformation relationship can be represented as $$\begin{array}{c} \text{CELL } Y \\ Ya \\ Yb \\ Yc \\ Y\alpha \\ Y\beta \\ Y\gamma \end{array} \quad \begin{array}{c} H \text{ Matrix} \\ \begin{bmatrix} h_{11} & h_{12} & h_{13} \\ h_{21} & h_{22} & h_{23} \\ h_{31} & h_{32} & h_{33} \end{bmatrix} \end{array} \quad \begin{array}{c} \text{CELL } Z \\ Za \\ Zb \\ Zc \\ Z\alpha \\ Z\beta \\ Z\gamma \end{array}$$

Figure 2A:
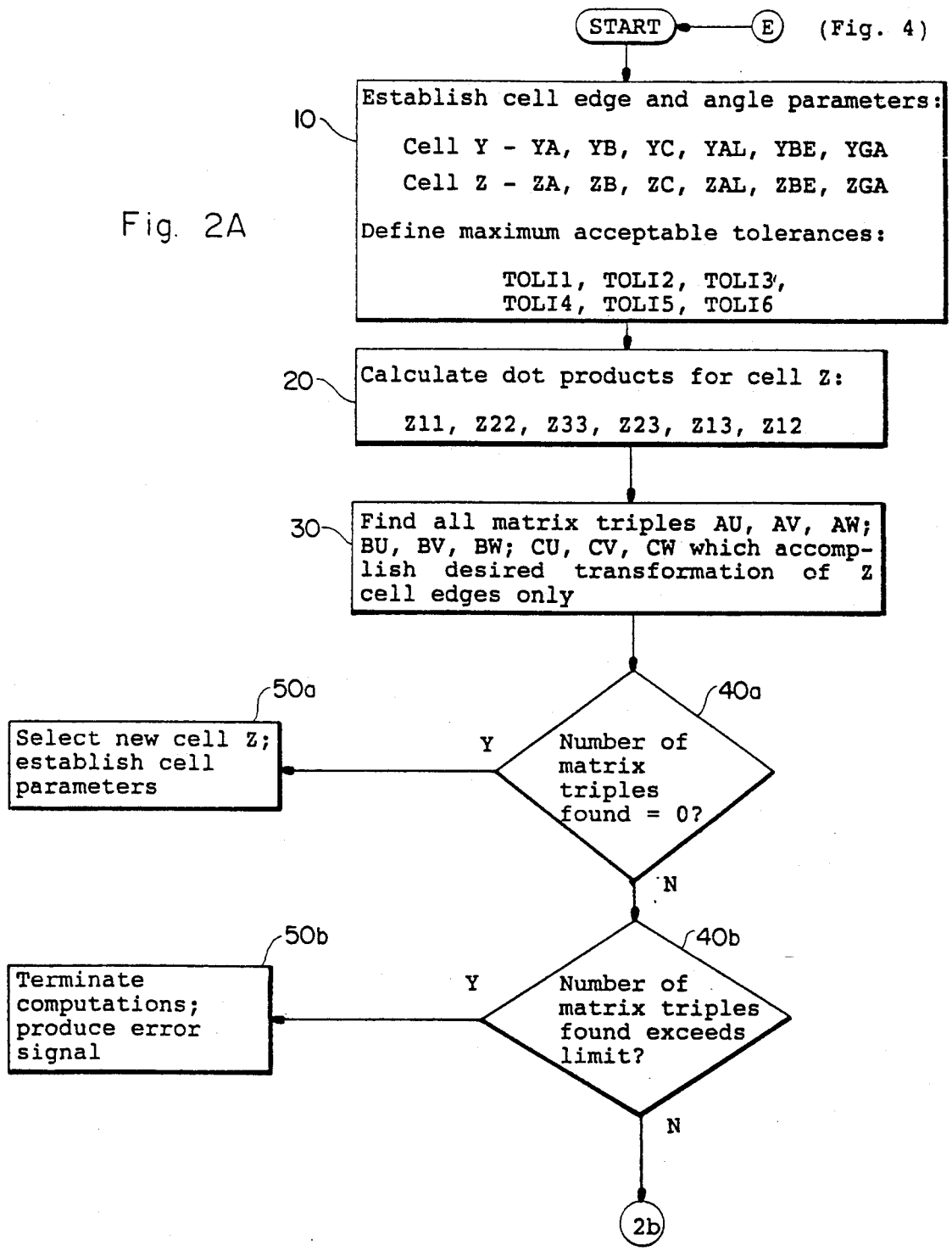
FIGS. 2A–2B are a flow chart of a preferred embodiment of the converse transformation matrix generation method of the present invention.
Figure 2B:
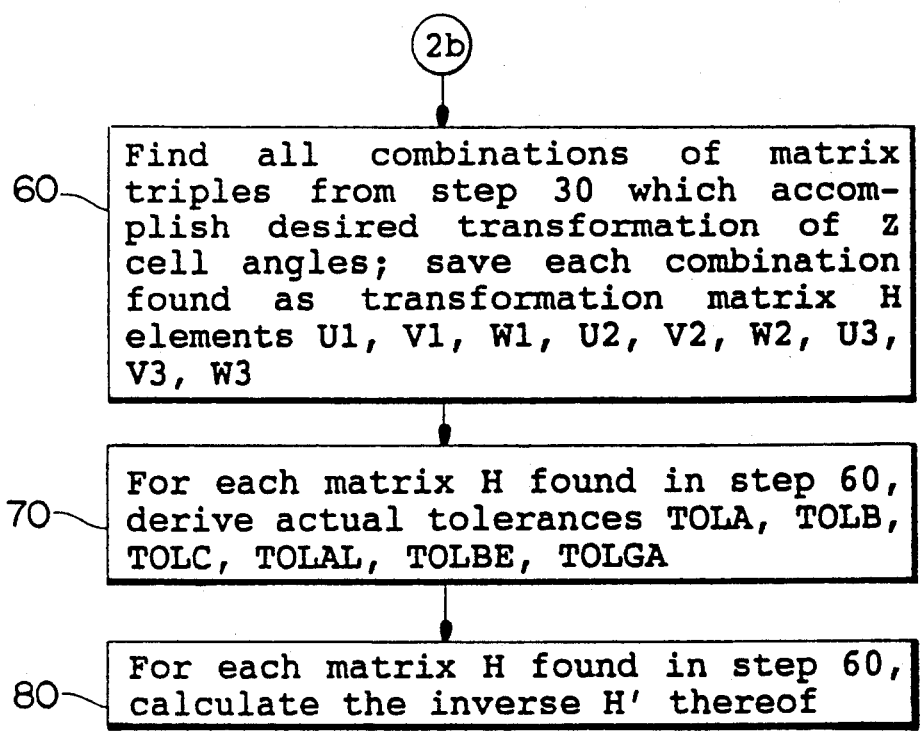

Referring to FIG. 2, a preferred form of the converse transformation matrix generation method of the present invention which is adapted for computer implementation will be described with reference to two primitive cells Y and Z, which can be the same cell if a symmetry analysis is being performed on a lattice structure. It will also be appreciated that when an unknown lattice structure is being identified, one of the cells may be derived from a database or the like of known lattice structures. In that case, cell Y defines a known lattice structure in the database, and cell Z defines the unknown lattice structure. Further, in the following description, the cell edge parameters a, b and c of cells Y and Z will be referred to as YA, YB, YC and ZA, ZB, ZC, respectively; the cell angle parameters $\alpha$, $\beta$ and $\gamma$ of the cells will be similarly referred to as YAL, YBE, YGA and ZAL, ZBE and ZGA, respectively. The maximum tolerances acceptable (input parameters) for relating transformed CELL Z to CELL Y will be referred to as TOLI1, TOLI2, TOLI3, TOLI4, TOLI5, TOLI6, respectively; whereas the *actual* tolerances found when relating transformed CELL Z to CELL Y will be referred to as TOLA, TOLB, TOLC, TOLAL, TOLBE, and TOLGA, respectively. By definition these actual tolerances constitute the tolerance matrix T:

$$T = \begin{array}{c} tol\ a\ tol\ b\ tol\ c \\ tol\ \alpha\ tol\ \beta\ tol\ \gamma \end{array}$$

The first step 10 of the transformation matrix generation method of the present invention is to establish the edge and angle parameters YA, YB, YC, YAL, YBE, YGA ZA, AB, ZC, ZAL, ZBE and ZGA of cells Y and Z, and to define the maximum acceptable tolerance values TOLI1, TOLI2, TOLI3, TOLI4, TOLI5 and TOLI6. It will be appreciated that the primitive cell parameters for an unknown lattice structure Z ca be experimentally measured using conventional techniques, such as x-ray diffractometry or analytical electron microscopy, for example. One preferred way to obtain cell parameter data for an unknown lattice structure is to determine two planes of diffraction data in reciprocal space. From the data on each plane and from the orientation of the two planes with respect to each other, a primitive cell in reciprocal space can be determined. The cell is then converted to direct space in Ångstrom units. Advantageously, the unknown lattice cell Z also is reduced in a conventional manner. Further, a reduced form of cell Y as well as cell Z is advantageously used. The use of reduced cells speeds computer processing and limits the matrix elements which need to be considered. As noted above, it is not necessary or even advantageous to determine a standard cell. Further, if the cell determined is not a primitive cell, but instead a supercell in reciprocal space (subcell in direct space) because diffraction nodes were missed, analysis of the lattice structure can still be carried out using the matrix approach of the present invention.

Maximum tolerance values are selected according to an assessment of the size of the experimental errors. By setting large limits (e.g., 1.0 and 6.0 for the cell edges and angles, respectively), all possible lattice relationships/symmetries may be obtained. It will be appreciated that the cell parameter and maximum tolerance values are stored as data in a computer for computer implementation of the transformation matrix generation method of the present invention.

The next step (step 20 in FIG. 2) is to calculate the dot products Z11, Z22, Z33, Z23, Z13 and Z12 for cell Z (i.e., A.A, B.B, C.C, B.C, A.C and A.B), as follows:

$$Z11 = ZA*ZA$$

$$Z22 = ZB*ZB$$

$$Z33 = ZC*ZC$$

$$Z23 = ZB*ZC*\cos(ZAL/\text{RADIAN})$$

$$Z13 = ZA*ZC*\cos(ZBE/\text{RADIAN})$$

$$Z12 = ZA*ZB*\cos(ZGA/\text{RADIAN})$$

where RADIAN=$360/2\pi$.

In step 30, all of the matrix triples AU, AV, AW; BU, BV, BW; and CU, CV; CW are respectively determined (in the manner described hereinbelow) which transform the Z cell edges ZA, ZB and ZC into the Y cell edges YA, YB and YC, respectively, within the respective specified tolerance values TOLI1, TOLI2 and TOLI3.

Next, the number of matrix triples determined in step 30 is tested in steps 40a and 40b to determine whether no matrix triples were found (step 40a) or a number of matrix triples were found exceeding a predetermined limit (e.g. 2000) (step 40b). If no matrix triples were found, further computations are terminated and a new cell Y is selected for comparison with cell Z in step 50a (when the identity of the lattice structure corresponding to cell Z is being sought). If too many matrix triples are found, further computations are terminated and an error signal is produced in step 50b.

If at least one set, but not an excessive number, of matrix triples are found in step 30, then all combinations of those matrix triples found in step 30 are determined in step 60 (in the manner described hereinbelow) which also transform the Z cell angles ZAL, ZBE and ZGA into the Y cell angles YAL, YBE and YGA, respectively, within the respective specified tolerance values TOLI4, TOLI5 and TOLI6. Each combination of matrix triples found is saved as the elements U1, V1, W1, U2, V2, W2, U3, V3, W3 of a transformation matrix H.

The actual tolerances TOLA, TOLB, TOLC, TOLAL, TOLBE, TOLGA for each transformation matrix H determined in step 60 are calculated in step 70, and the inverse H' of each matrix H is calculated in step 80.

Figure 3A:
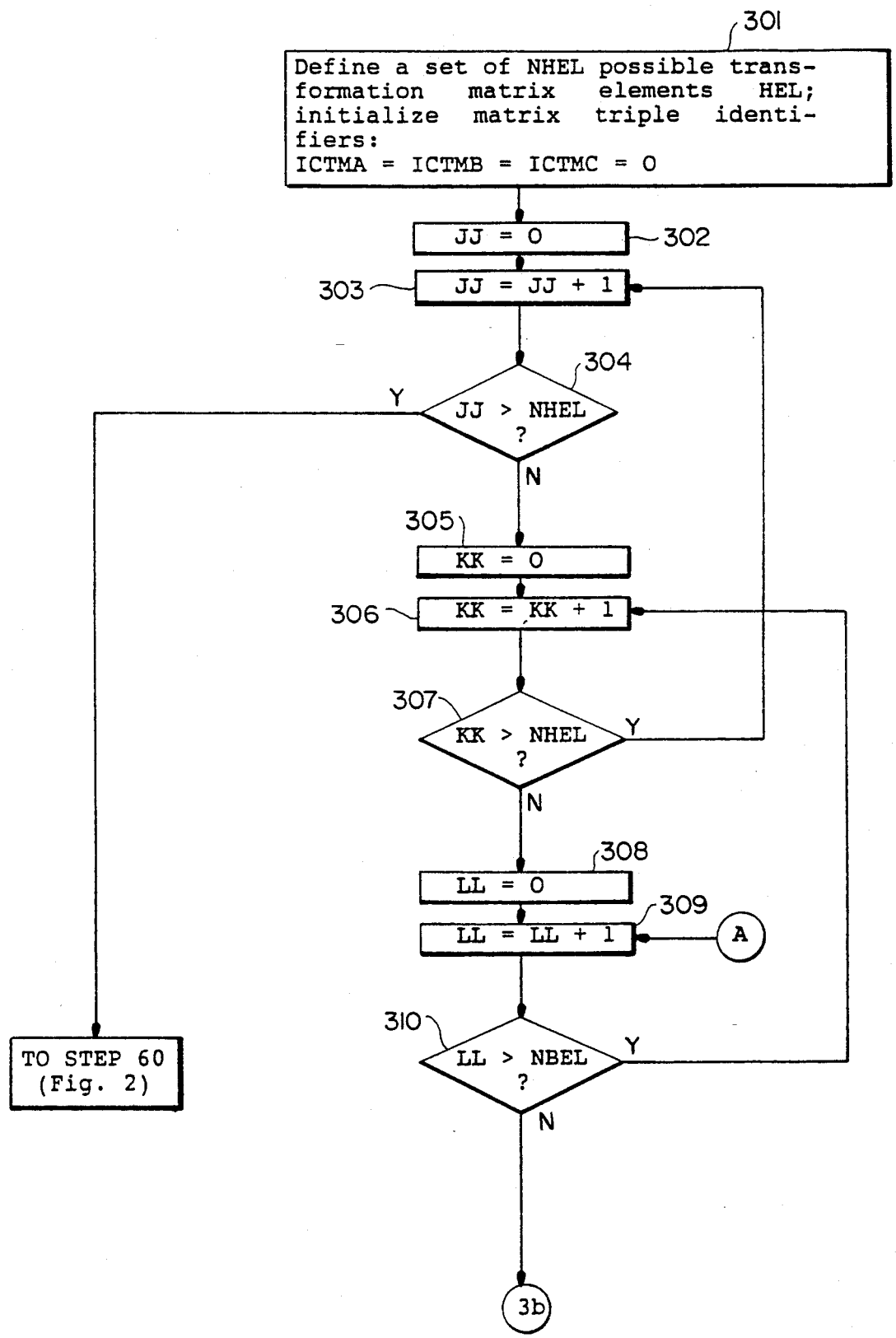
FIGS. 3A–3C are a more detailed flow chart of a preferred embodiment of step 60 shown in FIG. 2 which integrates steps 70 and 80 as part of step 60.
Figure 3B:
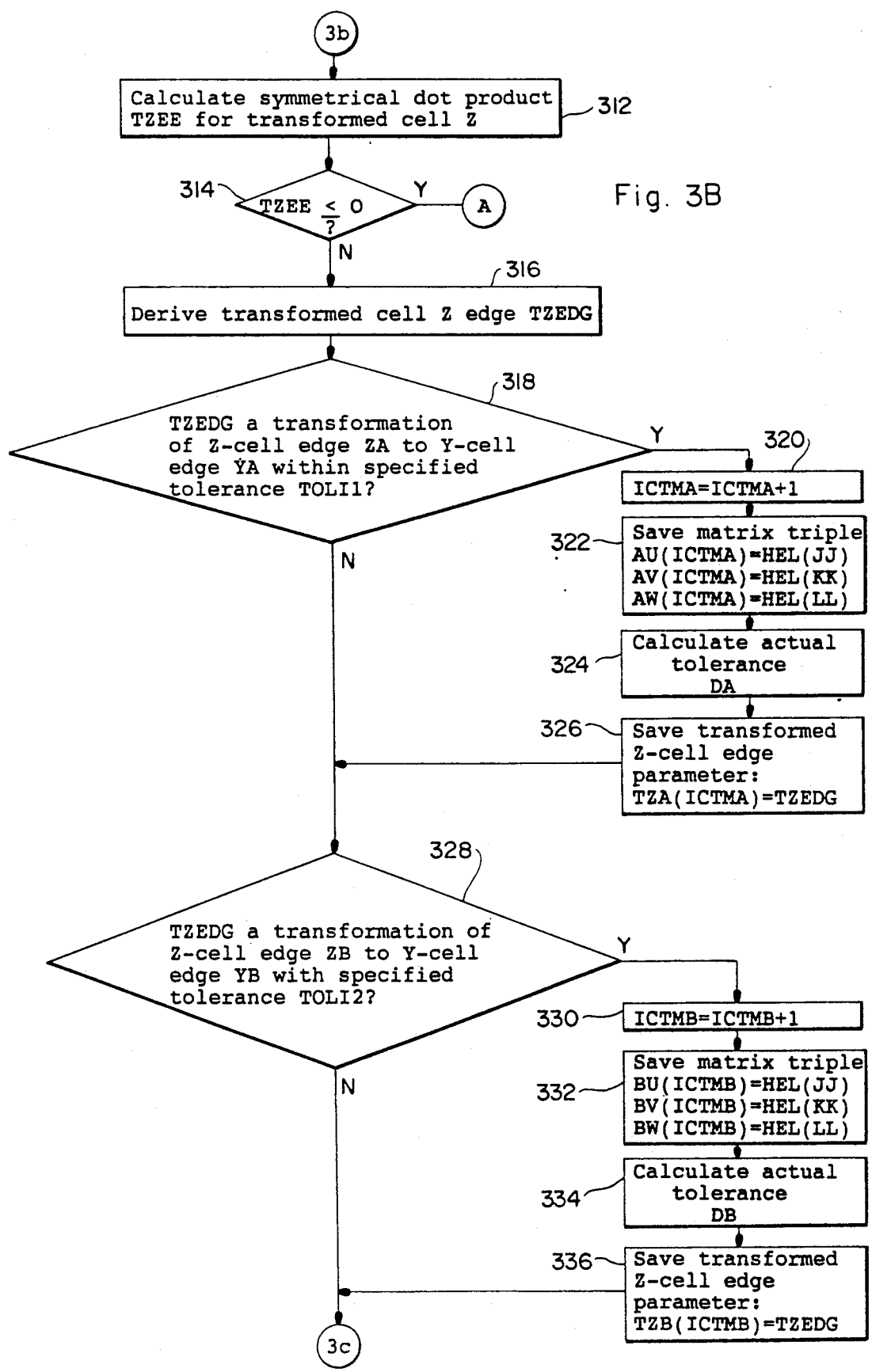
Figure 3C:
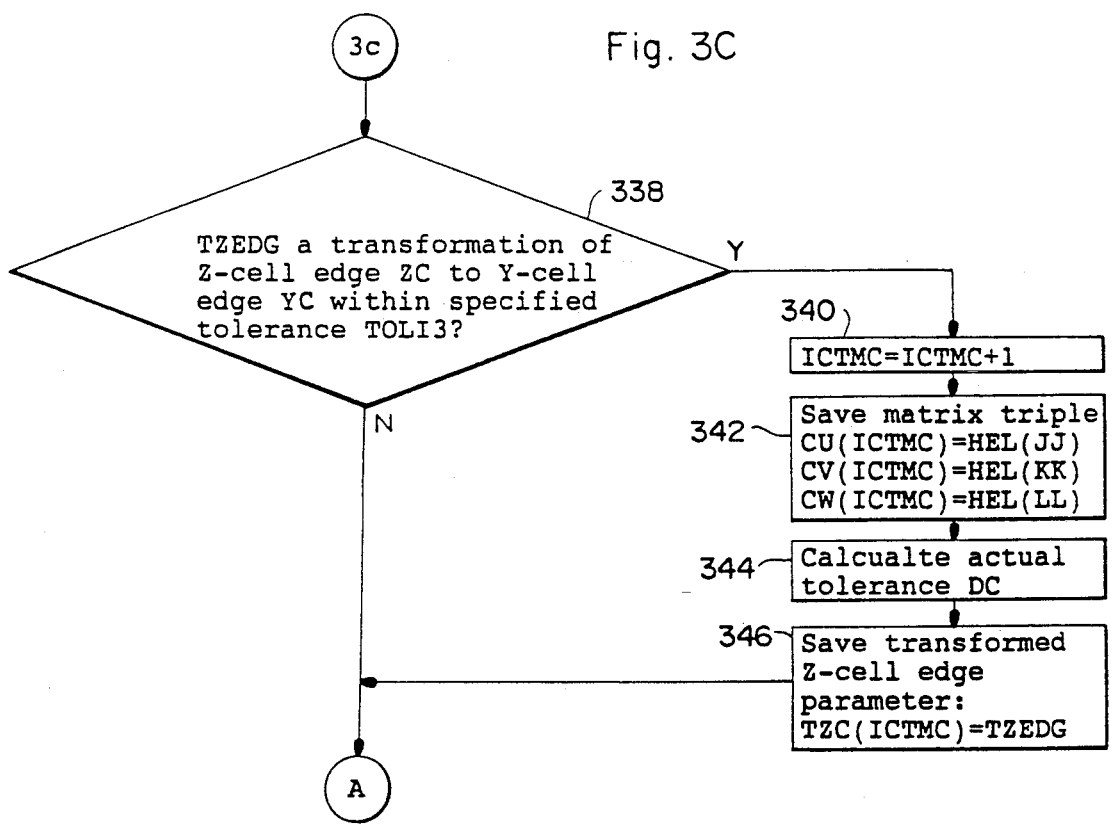

Referring to FIG. 3, a preferred method for determining the matrix triples in step 30 will now be described. First, in step 301, a set of a predetermined number NHEL of possible integer and rational number values HEL(JJ), HEL(KK), HEL(LL) (JJ, KK, LL=1,2 ... NHEL) for the elements of a transformation matrix H are defined (stored). A typical range of values HEL is $-6 \leq BEL \leq 6$, including both the integer values $\pm 1$, $\pm 2$, $\pm 3$, $\pm 4$, $\pm 5$, and $\pm 6$, and the non-integer rational number inverses thereof, i.e., $\pm \frac{1}{2}$, $\pm \frac{1}{3}$, $\pm \frac{1}{4}$, $\pm 1/5$ and $\pm 1/6$. The range of values HEL is normally selected based o the type of problem to be solved. With reduced versions of cells Y and Z, for example, the range of potential values for values HEL is reduced. In addition, variable indicies ICTMA, ICTMB and ICTMC, which are respectively used to identify the matrix triples AU, AV, AW; BU, BV, BW; and CU, CV, CW determined to transform the respective Z-cell edges into the corresponding Y-cell edges within the respective specified tolerances, as described hereinabove, are initialized to zero.

In steps 302-310, variable indices JJ, KK and LL for signifying individual ones of the values HEL and controlling iteration of computation loops are initialized, incremented and compared with NHEL in the sequence shown to provide first, second and third nested computation loops using successive combinations of HEL(JJ), HEL(KK) and HEL(LL) as described in more detail hereinbelow.

Since JJ, KK, and LL initially are not greater than NHEL, as determined in steps 304, 307 and 310, respectively, a symmetrical dot product TZEE for transformed cell Z is calculated in step 312 using values HEL(JJ), HEL(KK) and HEL(LL) and dot products Z11, Z22, Z33, Z23, Z13 and Z12 for cell Z calculated in step 20 (FIG. 2) as follows:

$$TZEE = HEL(JJ)*HEL(JJ)*Z11 + HEL(KK)*HEL(KK)*Z22 +$$

-continued $$HEL(LL)*HEL(LL)*Z33 + 2.0\ (HEL(KK)*HEL(LL)*Z23 +$$
$$HEL(JJ)*HEL(LL)*Z13 + HEL(JJ)*HEL(KK)*Z12)$$

It will be appreciated that the values HEL(JJ), HEL(KK) and HEL(LL) form a row of a transformation matrix and that the calculated dot product may correspond to A.A, B.B or C.C depending on the order of the matrix row in the final transformation matrix H.

Next, in step 314, dot product TZEE is tested to determine whether it is greater than zero. If not, no further computations are done using the current combination of values HEL, and the third computation loop comprising steps 309-346 is restarted using a new value of HEL(LL) by returning to step 309.

If TZEE>0, then a transformed edge for cell Z, TZEDG, is derived (step 316) as follows:

$$TZEDG = \sqrt{TZEE}$$

Then TZEDG is tested (step 318) to determine whether it constitutes a transformation of Z-cell edge ZA to Y-cell edge YA within the specified tolerance TOLI1 by determining whether:

$$(TOLI1 - |TZEDG - YA|) < 0.$$

If the determination in step 318 is TRUE (i.e., the foregoing inequality is FALSE) then the current values of HEL(JJ), HEL(KK) and HEL(LL) from which TZEDG was derived is a possible row in a transformation matrix H; and the counter ICTMA is thus incremented (step 320), and the values HEL(JJ), HEL(KK) and HEL(LL) are saved (step 322) as matrix triple AU(ICTMA), AV(ICTMA) and AW(ICTMA), respectively. A value DA(ICTMA)=TZEDG −YA representing the actual tolerance (difference) between the transformed Z cell edge A and the inputted Y-cell YA is also calculated and saved (step 324); together with a value TZA(ICTMA)=TZEDG as the transformed Z-cell edge a parameter (step 326). The computation then proceeds to step 328.

If a FALSE determination is made in step 318 (i.e., the inequality is TRUE), then TZEDG is similarly tested in step 328 to determine whether it constitutes a transformation of the Z-cell edge ZB to the Y-cell edge YB within the specified tolerance TOL12, i.e., whether (TOLI2− |TZEDG−YB|)<0. Similarly to steps 320-326, if the determination in step 328 is TRUE, then the counter ICTMB is incremented (step 330); the current values of HEL(JJ), HEL(KK) and HEL(LL) are saved (step 332) as matrix triple BU(ICTMB), BV(ICTMB), BW(ICTMB); values DB(ICTMB)=-TZEDG −YB, and TZB(ICTMB)=TZEDG are calculated and saved (steps 334-336); and the computation proceeds to step 338.

If a FALSE determination is made in step 328, then TZEDG is again similarly tested in step 338 with respect to Y-cell edge YC to determine whether (TOLI3− |TZEDG−YB|)<0. Similarly to steps 320-326 and 330-336, if the determination in step 338 is TRUE, then counter ICTMC is incremented (step 340); the current values of HEL(JJ), HEL(KK) and HEL(LL) are saved (step 342) as matrix triple CU(ICTMC), CV(ICTMC), CW(ICTMC); and values DC(ICTMC), and TZC(ICTMC)=TZEDG are calcuated and saved (steps 344-346). The third computation loop comprising steps 309-346 is then repeated using a new value of HEL(LL) by returning to step 309.

Similarly, if a FALSE determination is made in step 338, then the third computation loop comprising steps 309-346 is repeated using a new value of HEL(LL) by returning to step 309. The third computation loop is repeated using successive values HEL(LL) and the same values HEL(JJ) and HEL(KK) until step 310 determines that indicia LL>NHEL, in which case the second computation loop, comprising steps 306-346, is restarted using the next value of HEL(KK) and the first value HEL(LL) by returning to step 306. The second computation loop is then successively repeated for each new value HEL(KK) in conjunction with successive nested repetition of the third computation loop for each value HEL(LL) until step 307 determines that KK>NHEL, in which case the first computation loop, comprising steps 303-346, is restarted using the next value of HEL(JJ) by returning to step 303. The first computation loop is successively repeated for each new value HEL(JJ) in conjunction with successive nested repetition of the second and third computation loops as before. When step 308 determines that JJ>NHEL, then all combinations of HEL(JJ), HEL(KK) and HEL(LL) have been used to determine all matrix triples which potentially constitute elements of a desired transformation matrix H, and the determination of step 60 (FIG. 2) is commenced.

Figure 4A:
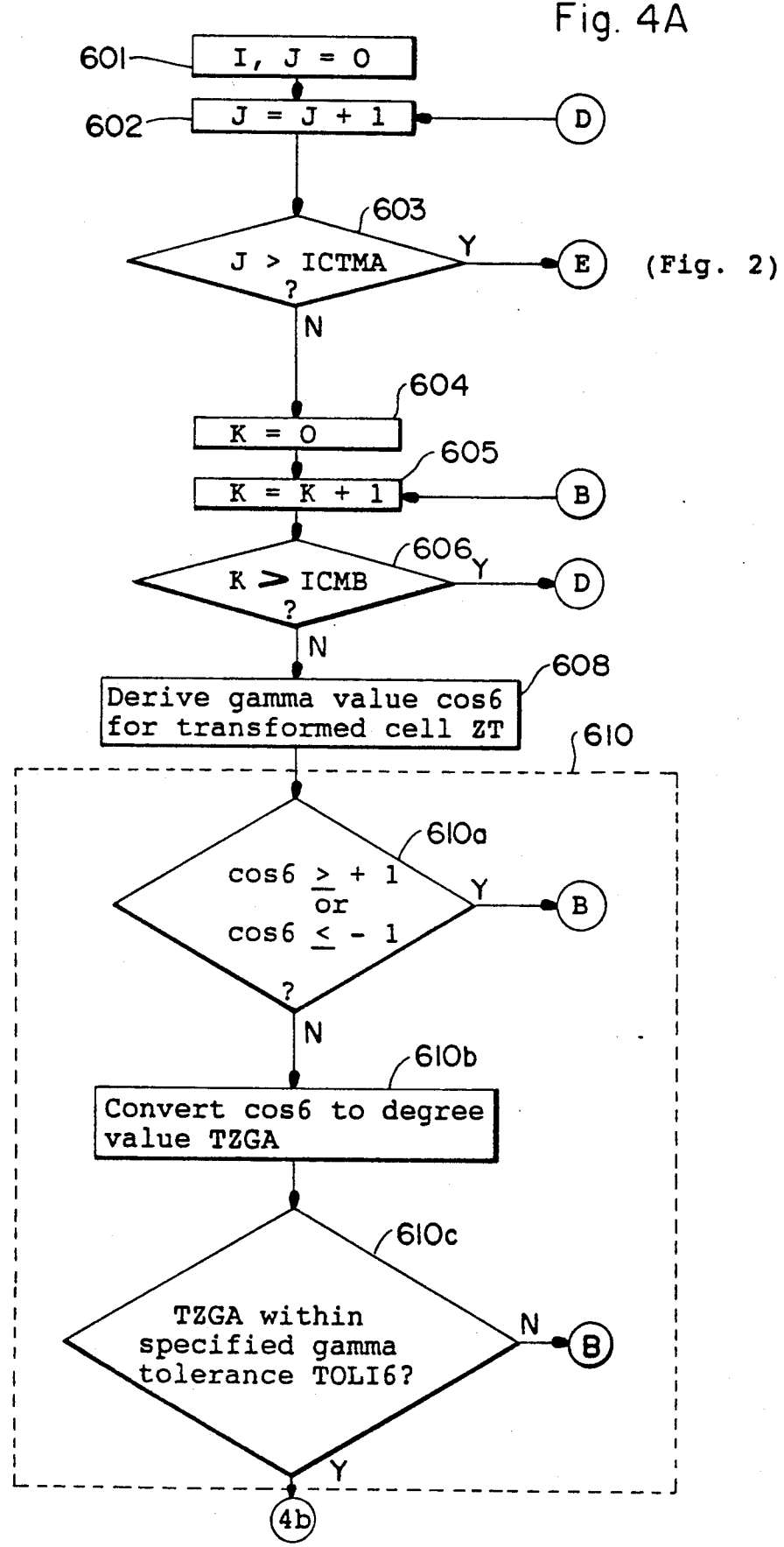
FIGS. 4A–4C are a more detailed flow chart of a preferred embodiment of step 30 shown in FIG. 2.
Figure 4B:
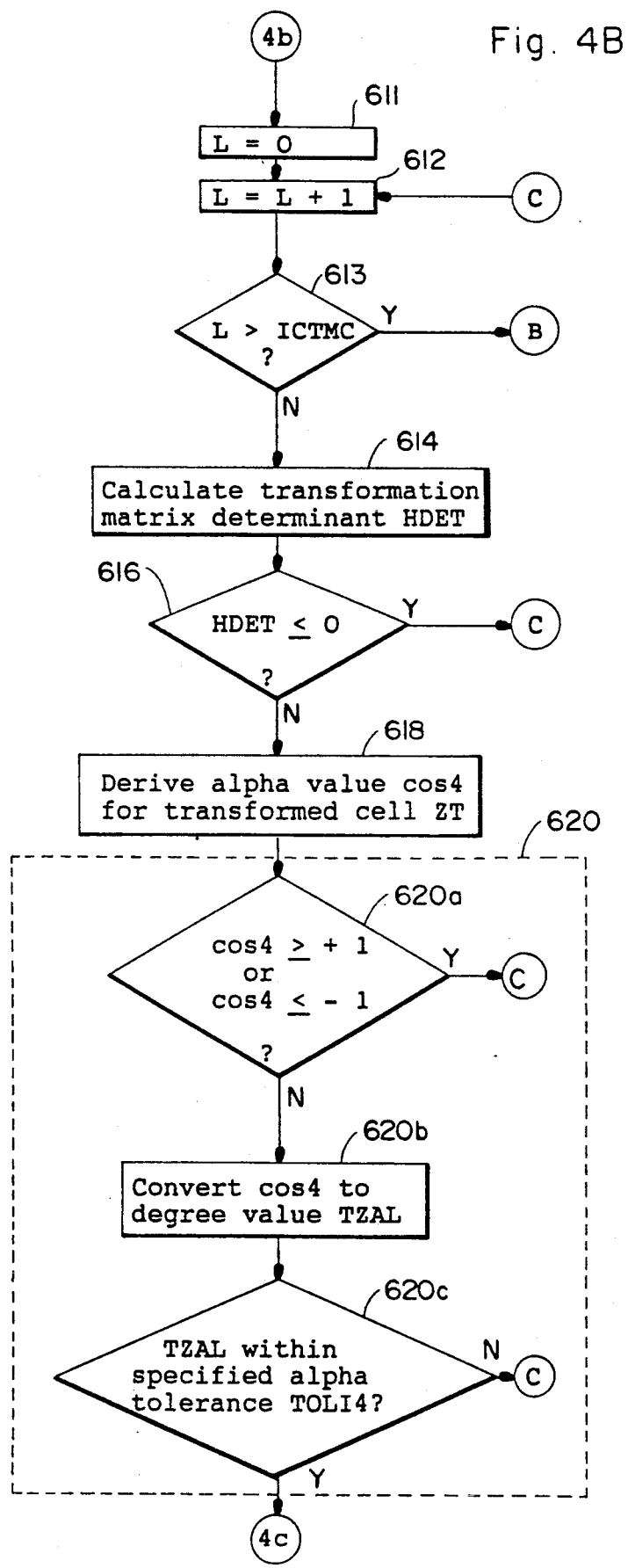
Figure 4C:
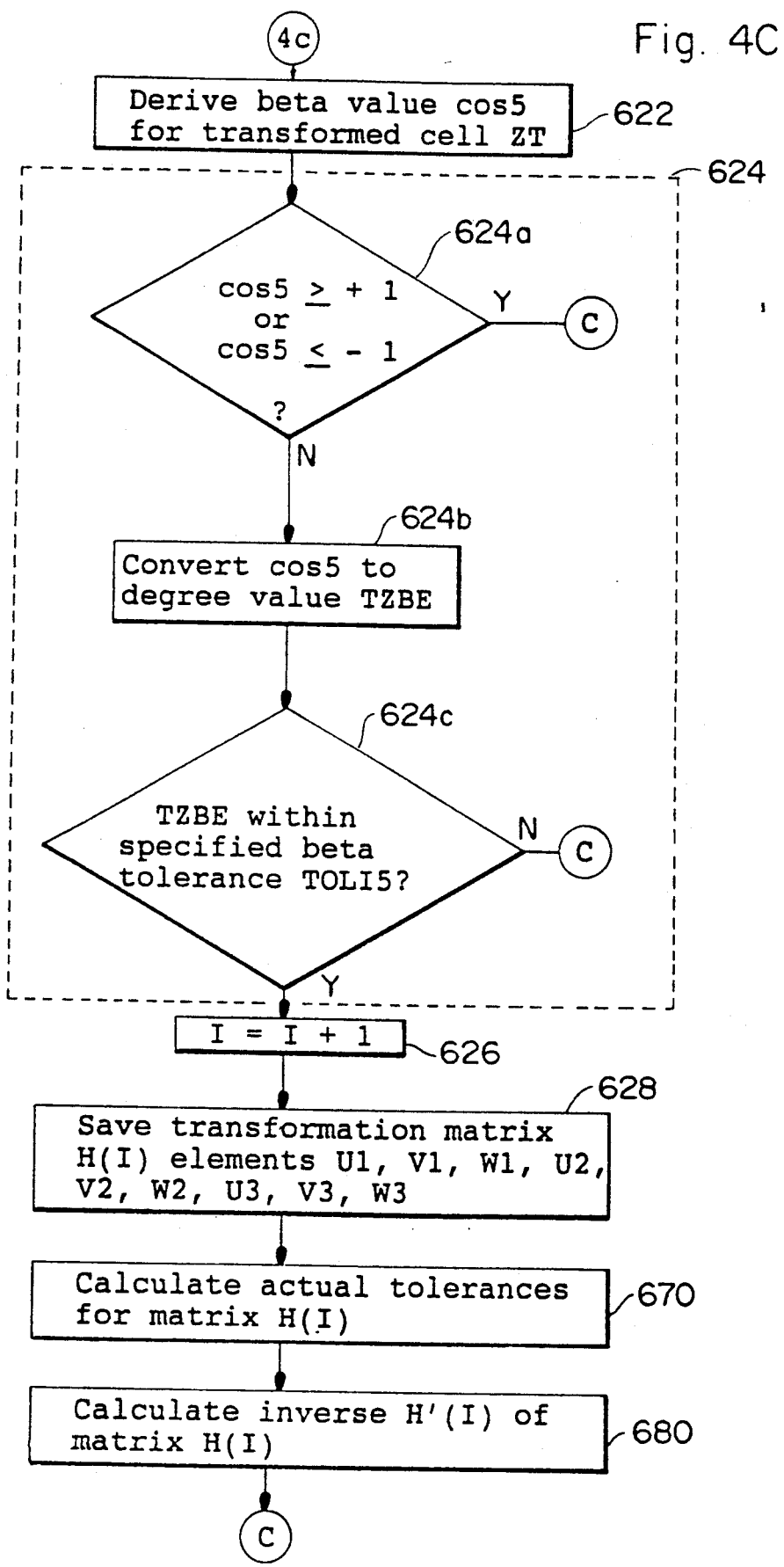

Referring to FIG. 4, a preferred method of performing step 60 (determining which combinations of the matrix triples found in step 30 also transform the Z-cell angles into the corresponding Y-cell angles within the specified tolerances) will now be described. In steps 601-606, variable indices I, J and K are initialized, and indices J and K are incremented and compared with ICTMA and ICTMB, respectively, in the sequence shown to provide first and second nested computation loops. Since J initially is not greater than ICTMA and K initially is not greater than ICTMB, step 608 is then performed, wherein a gamma value cos6 for transformed cell TZ is derived by first calculating a first unsymmetrical dot product TZEF1 as follows:

$$TZEF1 = AU(J)*BU(K)*Z11 + AV(J)*BV(K)*Z22 +$$
$$AW(J)*BW(K)*Z33 + (AV(J)*BW(K) + AW(J)*BV(K))*Z23 +$$
$$(AU(J)*BW(K) + AW(J)*BU(K))*Z13 + (AU(J)*BV(K) +$$
$$AV(J)*BU(K))*Z12$$

Gamma value cos6 is then calculated as follows:

$$\cos 6 = TZEF1/(TZA(J)*TZB(K)).$$

Gamma value cos6 is then tested (step 610) to determine whether $\cos 6 \geq 1$ or $\cos 6 \leq (-1)$ (step 610a); and if FALSE, cos6 is converted to degrees by computing TZGA = $(\cos^{-1}(\cos 6))$*RADIAN (step 610b), and further tested (step 610c) to determine whether the current pair of matrix triples transforms Z-cell angle ZGA to Y-cell angle YGA within the specified tolerance TOLI6 by determining whether:

$$TOLI6 - |(TZGA - YGA)| < 0$$

If the determination in step 610a is TRUE (i.e., cos6 is not within the ±1 range), or if the determination in step 610c is FALSE (i.e., the inequality is TRUE), then no further computations are performed with the current pair of matrix triples AU(J), AV(J), AW(J) AND BU(K), BV(K), BW(K), and the second computation loop, comprising steps 605-680 is restarted using an incremented value of K by returning to step 605.

If the determination in step 610c is TRUE (i.e., the inequality is FALSE), then a third computation loop comprising steps 611-680 is commenced by initializing variable indicia L, incrementing indicia L and testing L to determine whether it is greater than ICTMC in successive steps 611-613 as shown.

Next, the transformation matrix determinant HDET is calculated (step 614) using the current set of matrix triples AU(J), AV(J), AW(J); BU(K), BV(K), BW(K); CU(L), CV(L); CW(L) as follows:

$$HDET = AU(J)*BV(K)*CW(L) + AV(J)*BW(K)*CU(L) +$$
$$AW(J)*BU(K)*CV(L) - CU(L)*BV(K)*AW(J) -$$
$$CV(L)*BW(K)*AU(J) - CW(L)*BU(K)*AV(J)$$

Determinant HDET is then tested (step 616) to determine whether HDET≤0. If the determination is TRUE, then no further computations are performed using the current set of matrix triples, and the third computation loop is restarted by returning to step 612.

If the determination in step 616 is FALSE, then an alpha value cos4 is calculated (step 618) similarly to gamma value cos6 by calculating a second unsymmetrical dot product TZEF2=BU(K)*CU(L)*Z11+BV(K)*CV(L)*Z22+BW(K)*CW(L)*Z33+(BV(K)*CW(L)+BW(K)*CV(L))*Z23+(BU(K)*CW(L)+BW(K)*CU(L))*Z13+(BU(K)*CV(L)+BV(K)*CU(L))* Z12; and then setting cos4=TZEF2/(TZB(K)*TZC(L)). Alpha value cos4 is then tested in step 620 similarly to the tests performed on gamma value cos6 in step 610. As in the case of gamma value cos6, if the determination in step 620a is that cos4 is not within the ±1 range or if the determination in step 620c is FALSE, then no further computations are performed with the current set of matrix triples and the third computation loop is restarted, by returning to step 612.

If the determination in step 620c is TRUE, then a beta value cos5 is calculated and tested similarly to alpha value cos4 in steps 622-624c, with:

$$TZEF3 = AU(J)*CU(L)*Z11 + (AV(J)*CV(L)*Z22 +$$
$$AW(J)*CW(L)*Z33 + (AV(J)*CW(L) +$$
$$AW(J)*CV(L))*Z23 + (AU(J)*CW(L) +$$
$$AW(J)*CU(L))*Z13 + (AU(J)*CV(L) +$$
$$AV(J)*CU(L))*Z12; \text{ and}$$
$$\cos 5 = TZEF3/(TEA(J)*TZC(L))$$

As in the cases of gamma value cos6 and alpha value cos4, if the determination in step 624a is that cos5 is not within the ±1 range or if the determination in step 624c is FALSE, then no further computations are performed with the current set of matrix triples and the third computation loop is restarted, by returning to step 612.

If the determination in step 624c is TRUE, then the current set of three matrix triples constitutes a desired transformation matrix H. Matrix variable I is incremented (step 626), and the matrix triple elements are saved (stored) (step 628) as transformation matrix H(I) elements U1, VI, W1, U2, V2, W2, U3, V3 and W3 as follows:

| | |
|---|---|
| UI | = AU(J) |
| VI | = AV(J) |
| W1 | = AW(J) |
| U2 | = BU(K) |
| V2 | = BV(K) |
| W2 | = BW(K) |
| U3 | = CU(L) |
| V3 | = CV(L) |
| W3 | = CW(L) |

Preferably, as part of the same computation loop, steps 70 and 80 (FIG. 2) described hereinabove are also performed as steps 670 and 680, respectively; with the actual tolerances for matrix H(I) being calculated as follows:

$$TOLA = DA(J)$$

$$TOLB = DB(K)$$

$$TOLC = DC(L)$$

$$TOLGA = TZAL - YAL$$

$$TOLBE = TZBE - YBE$$

$$TOLGA = TZGA - YGA;$$

and the elements UI1, VI1, WI1, UI2, VI2, WI2, UI3, VI3, WI3 of the inverse H'(I) of the transformation matrix H(I) being calculated as follows:

$$UI1 = (V2*W3 - V3*W2)/HDET$$

$$VI1 = -(V1*W3 - V3*W1)/HDET$$

$$WI1 = (V1*W2 - V2*W1)/HDET$$

$$UI2 = -(U2*W3 - U3*W2)/HDET$$

$$VI2 = (U1*W3 - U3*W1)/HDET$$

$$WI2 = -(U1*W2 - U2*W1)/HDET$$

$$UI3 = (U2*V3 - U3*V2)/HDET$$

$$VI3 = -(U1*V3 - U3*V1)/HDET$$

$$WI3 = (U1*V2 - U2*V1)/HDET$$

The third computation loop of steps 612–680 is then restarted by returning to step 612, until step 613 determines that L>ICTMC, in which case the second computation loop of steps 605–680 is repeated with an incremented K indicia by returning to step 605. The second computation loop (which includes the nested third computation loop of steps 612–680) is repeated until step 606 determines that K>ICTMB, in which case the first computation loop of steps 602–680 is repeated with an incremented J indicia by returning to step 602. This computation loop (which includes the nested second and third computation loops) is repeated until step 605 determines that J>ICTMA, in which case the transformation matrix determination method is completed and all of the desired transformation matrices H(I) have been generated, and the transformation matrix determination method can be restarted with a new cell Z and/or cell Y.

A commented listing of a computer program which implements the methods shown in FIGS. 2–4 follows. (The program is written to print each matrix H and the associated inverse, actual tolerances and matrix determinant at the end of the third computation loop of step 60. Accordingly, no indicia I is provided for storing data for multiple matrices H(I) as in the flow chart of FIG. 4.) The program is written in ANSI standard FORTRAN, and is designed to be transportable and readily encoded for execution on all types of computers, whether independently or integrated in other programs, such as, for example, control programs associated with diffractometers. It will be appreciated that the program could be shortened by replacing portions of the code with calls to subroutines. However, such calls significantly increase the CPU execution time.

```
            COPYRIGHT 1989 U.S. Secretary of Commerce, as represented by the National
            Institute for Standards and Technology, on behalf of the United States of
            America 1218        SUBROUTINE HMATRX
1219        DIMENSION AU(2000),AV(2000),AW(2000)
1220        DIMENSION BU(2000),BV(2000),BW(2000)
1221        DIMENSION CU(2000),CV(2000),CW(2000)
1222        DIMENSION DA(2000),DB(2000),DC(2000)
1223        DIMENSION TZA(2000),TZB(2000),TZC(2000)
1224   C
1225        COMMON /HCELL1/ YA,YB,YC,YAL,YBE,YGA,YV
1226        COMMON /HCELL2/ ZA,ZB,ZC,ZAL,ZBE,ZGA,ZV
1227        COMMON /HDET1/ HDET
1228        COMMON /HELEM1/ NHEL
1229        COMMON /HELEM2/ HEL(99)
1230        COMMON /HTOL1/ TOLI1,TOLI2,TOLI3,TOLI4,TOLI5,TOLI6
1231        COMMON /HTOL2/ TOLA,TOLB,TOLC,TOLAL,TOLBE,TOLGA
1232   C
1233        COMMON /CONST1/ RADIAN
1234        COMMON /INVER1/ UI1,VI1,WI1,UI2,VI2,WI2,UI3,VI3,WI3
1235        COMMON /MATR1/ U1,V1,W1,U2,V2,W2,U3,V3,W3
1236        COMMON /UNIT2/ IUNITB
```

```
1237  C**
1238        COMMON /CK05/ ICK051
1239  C*
1240  C
1241  C
1242  C     SUBROUTINE 'HMATRX' ...
1243  C
1244  C        CALCULATES THE MATRICES (H) RELATING TWO OR
1245  C        MORE LATTICES
1246  C
1247  C        THE TRANSFORMATION IS DEFINED BY THE EQUATION
1248  C                      Y = (H MATRIX) Z
1249  C
1250  C
1251  C     HEL = INPUT MATRIX ELEMENT - A POSSIBLE ELEMENT IN A MATRIX H
1252  C     NHEL = NUMBER OF INPUT MATRIX ELEMENTS
1253  C     U1,V1,W1,U2,V2,W2,U3,V3,W3 = A TRANSFORMATION MATRIX RELATING
1254  C        Z TO Y WITHIN THE SPECIFIED TOLERANCES - BY DEFINITION
1255  C        THIS IS A MATRIX H
1256  C     UI1,VI1,WI1,UI2,VI2,WI2,UI3,VI3,WI3 = INVERSE OF MATRIX H
1257  C     HDET = H MATRIX DETERMINANT
1258  C
1259  C     YA,YB,YC,YAL,YBE,YGA = INPUT CELL PARAMETERS FOR CELL Y
1260  C     ZA,ZB,ZC,ZAL,ZBE,ZGA = INPUT CELL PARAMETERS FOR CELL Z
1261  C     Z11,Z22,Z33,Z23,Z13,Z12 = DOT PRODUCTS (A.A B.B C.C
1262  C        B.C A.C A.B) FOR CELL Z
1263  C
1264  C     AU,AV,AW = MATRIX TRIPLE TRANSFORMING A-CELL EDGE OF Z TO
1265  C        YA WITHIN THE SPECIFIED TOLERANCE (TOLI1)
1266  C     DA = DIFFERENCE BETWEEN A-CELL EDGES (TRANSFORMED Z - Y)
1267  C     ICTMA = NUMBER OF MATRIX TRIPLES SAVED (DIMENSION OF ARRAYS
1268  C        AU,AV,AW,DA,TZA)
1269  C     BU,BV,BW,DB,ICTMB = ANALOGOUS TO DEFINITIONS FOR CELL EDGE A
1270  C     CU,CV,CW,DC,ICTMC = ANALOGOUS TO DEFINITIONS FOR CELL EDGE A
1271  C
1272  C     TZA,TZB,TZC,TZAL,TZBE,TZGA = TRANSFORMED CELL PARAMETERS FOR
1273  C        Z (TRANSFORMED BY POSSIBLE ROW(S) IN MATRIX H)
1274  C     TZEDG = A OR B OR C FOR TRANSFORMED CELL Z
1275  C     TZEE = SYMMETRICAL DOT PRODUCTS (A.A OR B.B OR C.C) FOR
1276  C        TRANSFORMED CELL Z
1277  C     TZEF = UNSYMMETRICAL DOT PRODUCTS (B.C OR A.C OR A.B) FOR
1278  C        TRANSFORMED CELL Z
1279  C
1280  C     TOLI1,TOLI2,TOLI3,TOLI4,TOLI5,TOLI6 = INPUT VALUES FOR
1281  C        MAXIMUM TOLERANCE ACCEPTABLE FOR RELATING TRANSFORMED
1282  C        CELL Z TO CELL Y
1283  C     TOLA,TOLB,TOLC,TOLAL,TOLBE,TOLGA = ACTUAL TOLERANCES FOUND
1284  C        WHEN RELATING TRANSFORMED CELL Z TO CELL Y - BY
1285  C        DEFINITION, THIS IS THE TOLERANCE MATRIX
1286  C
1287  C
1288  C
1289  C     COMPUTING NOTE (1987) - THIS ROUTINE COULD BE SHORTENED BY
1290  C        REPLACING CODE WITH CALLS TO SUBROUTINES.  HOWEVER, THESE
1291  C        CALLS *SIGNIFICANTLY* INCREASE THE CPU TIME.
1292  C
1293  C
1294  C     ---   CALCULATE DOT PRODUCTS FOR CELL Z
1295        Z11 = ZA*ZA
1296        Z22 = ZB*ZB
1297        Z33 = ZC*ZC
1298        Z23 = ZB*ZC*COS(ZAL/RADIAN)
1299        Z13 = ZA*ZC*COS(ZBE/RADIAN)
1300        Z12 = ZA*ZB*COS(ZGA/RADIAN)
1301  C
```

```
1302  C          — INITIALIZE VARIABLES
1303             ICTMA = 0
1304             ICTMB = 0
1305             ICTMC = 0
1306  C
1307  C          — FIND MATRIX TRIPLES WHICH SATISFY TRANSFORMATION
1308  C             OF CELL EDGES (ONLY)
1309             DO 270 JJ = 1,NHEL
1310               DO 260 KK = 1,NHEL
1311                 DO 250 LL = 1,NHEL
1312  C
1313  C             — CALCULATE SYMMETRICAL DOT PRODUCTS FOR TRANSFORMED
1314  C                CELL Z.  INPUT MATRIX ELEMENTS ARE USED TO FORM A
1315  C                ROW OF A TRANSFORMATION MATRIX.  DOT PRODUCT MAY BE
1316  C                A.A, B.B, OR C.C DEPENDING ON ORDER OF MATRIX
1317  C                ROW IN FINAL TRANSFORMATION MATRIX H.
1318                  TZEE =  HEL(JJ)*HEL(JJ)*Z11 + HEL(KK)*HEL(KK)*Z22 +
1319        $                 HEL(LL)*HEL(LL)*Z33 +
1320        $              2.0*(HEL(KK)*HEL(LL)*Z23 + HEL(JJ)*HEL(LL)*Z13 +
1321        $                 HEL(JJ)*HEL(KK)*Z12)
1322  C
1323                  IF(TZEE.LE.0.0) GO TO 240
1324  C
1325  C             — CALCULATE TRANSFORMED CELL EDGE FOR CELL Z
1326                  TZEDG = SQRT(TZEE)
1327  C
1328  C
1329  C
1330  C             — TEST WHETHER MATRIX TRIPLE TRANSFORMS A-CELL
1331  C                EDGE FOR Z TO YA WITHIN THE SPECIFIED TOLERANCE
1332                  IF((TOLI1-ABS(TZEDG-YA)).LT.0.0) GO TO 200
1333  C
1334  C                — MATRIX TRIPLE IS A POSSIBLE ROW IN A
1335  C                   MATRIX H. SAVE MATRIX ROW, ACTUAL
1336  C                   TOLERANCE, TRANSFORMED CELL EDGE FOR Z
1337                    ICTMA = ICTMA + 1
1338  C
1339                    AU(ICTMA) = HEL(JJ)
1340                    AV(ICTMA) = HEL(KK)
1341                    AW(ICTMA) = HEL(LL)
1342                    DA(ICTMA) = TZEDG - YA
1343                    TZA(ICTMA) = TZEDG
1344        200       CONTINUE
1345  C
1346  C
1347  C
1348  C             — TEST WHETHER MATRIX TRIPLE TRANSFORMS B-CELL
1349  C                EDGE FOR Z TO YB WITHIN THE SPECIFIED TOLERANC
1350                  IF((TOLI2-ABS(TZEDG-YB)).LT.0.0) GO TO 210
1351  C
1352  C                — MATRIX TRIPLE IS A POSSIBLE ROW IN A
1353  C                   MATRIX H, SAVE MATRIX ROW, ACTUAL
1354  C                   TOLERANCE, TRANSFORMED CELL EDGE FOR Z
1355                    ICTMB = ICTMB + 1
1356  C
1357                    BU(ICTMB) = HEL(JJ)
1358                    BV(ICTMB) = HEL(KK)
1359                    BW(ICTMB) = HEL(LL)
1360                    DB(ICTMB) = TZEDG - YB
1361                    TZB(ICTMB) = TZEDG
1362        210       CONTINUE
1363  C
1364  C
1365  C
1366  C             — TEST WHETHER MATRIX TRIPLE TRANSFORMS C-CELL
1367  C                EDGE FOR Z TO YC WITHIN THE SPECIFIED TOLERANC
1368                  IF((TOLI3-ABS(TZEDG-YC)).LT.0.0) GO TO 220
```

```
1369  C
1370  C                       —— MATRIX TRIPLE IS A POSSIBLE ROW IN A
1371  C                          MATRIX H. SAVE MATRIX ROW, ACTUAL
1372  C                          TOLERANCE, TRANSFORMED CELL EDGE FOR Z
1373                           ICTMC = ICTMC + 1
1374  C
1375                           CU(ICTMC) = HEL(JJ)
1376                           CV(ICTMC) = HEL(KK)
1377                           CW(ICTMC) = HEL(LL)
1378                           DC(ICTMC) = TZEDG - YC
1379                           TZC(ICTMC) = TZEDG
1380      220              CONTINUE
1381  C
1382  C
1383      240          CONTINUE
1384  C
1385      250      CONTINUE
1386      260    CONTINUE
1387      270 CONTINUE
1388  C
1389  C**
1390  C          —— FOR CHECKING ... PRINT NUMBER OF MATRIX ROWS SATISFYING
1391  C             TRANSFORMATION OF CELL EDGES A,B,C (ONLY), RESPECTIVELY
1392           IF(ICK051.EQ.1) WRITE(IUNITB,9500) ICTMA,ICTMB,ICTMC
1393  C*
1394  C
1395  C          —— IF NO MATRIX TRIPLES ARE FOUND THAT TRANSFORM
1396  C             CELL EDGES FOR Z TO Y, GO TO NEXT PROBLEM
1397           IF(ICTMA.LE.0.OR.ICTMB.LE.0.OR.ICTMC.LE.0) GO TO 900
1398  C
1399  C          —— IF TOO MANY MATRIX TRIPLES ARE GENERATED,
1400  C             WRITE ERROR MESSAGE AND STOP PROGRAM EXECUTION
1401           IF(ICTMA.LE.2000.AND.ICTMB.LE.2000.AND.ICTMC.LE.2000) GO TO 300
1402              WRITE(IUNITB,6000)
1403              STOP
1404      300 CONTINUE
1405  C
1406  C
1407  C          —— STARTING WITH MATRIX TRIPLES SATISFYING TRANSFORMATION
1408  C             OF CELL EDGES (FOR Z TO Y), DETERMINE WHICH COMBINATIONS
1409  C             ALSO TRANSFORM CELL ANGLES
1410           DO 565 J = 1,ICTMA
1411              DO 555 K = 1,ICTMB
1412  C
1413  C                —— CALCULATE GAMMA FOR TRANSFORMED CELL Z
1414  C                   AND CHECK WHETHER IT IS WITHIN
1415  C                   SPECIFIED TOLERANCES
1416                 TZEF = AU(J)*BU(K)*Z11 + AV(J)*BV(K)*Z22 +
1417       $                AW(J)*BW(K)*Z33 +
1418       $                (AV(J)*BW(K) + AW(J)*BV(K))*Z23 +
1419       $                (AU(J)*BW(K) + AW(J)*BU(K))*Z13 +
1420       $                (AU(J)*BV(K) + AV(J)*BU(K))*Z12
1421  C
1422  C
1423                 COS6 = TZEF/(TZA(J)*TZB(K))
1424                 IF(COS6.GE.1.0.OR.COS6.LE.-1.0) GO TO 550
1425                    TZGA = (ACOS(COS6))*RADIAN
1426                    IF((TOL16-ABS(TZGA-YGA)).LT.0.0) GO TO 550
1427  C
1428                 DO 545 L = 1,ICTMC
1429  C
1430  C                   —— DETERMINANT OF A MATRIX H WILL BE POSITIVE -
1431  C                      IF NOT, CHECK NEXT COMBINATION OF MATRIX TRIPLE
1432                    HDET = AU(J)*BV(K)*CW(L) + AV(J)*BW(K)*CU(L) +
1433       $                   AW(J)*BU(K)*CV(L) - CU(L)*BV(K)*AW(J) -
1434       $                   CV(L)*BW(K)*AU(J) - CW(L)*BU(K)*AV(J)
```

```
1435   C
1436                    IF(HDET.LE.0.0) GO TO 540
1437   C
1438   C               —— CALCULATE ALPHA FOR TRANSFORMED CELL Z
1439   C                  AND CHECK WHETHER IT IS WITHIN
1440   C                  SPECIFIED TOLERANCES
1441                    TZEF = BU(K)*CU(L)*Z11 + BV(K)*CV(L)*Z22 +
1442        $                  BW(K)*CW(L)*Z33 +
1443        $                  (BV(K)*CW(L) + BW(K)*CV(L))*Z23 +
1444        $                  (BU(K)*CW(L) + BW(K)*CU(L))*Z13 +
1445        $                  (BU(K)*CV(L) + BV(K)*CU(L))*Z12
1446   C
1447   C
1448                    COS4 = TZEF/(TZB(K)*TZC(L))
1449                    IF(COS4.GE.1.0.OR.COS4.LE.-1.0) GO TO 540
1450                    TZAL = (ACOS(COS4))*RADIAN
1451                    IF((TOLI4-ABS(TZAL-YAL)).LT.0.0) GO TO 540
1452   C
1453   C               —— CALCULATE BETA FOR TRANSFORMED CELL Z
1454   C                  AND CHECK WHETHER IT IS WITHIN
1455   C                  SPECIFIED TOLERANCES
1456                    TZEF = AU(J)*CU(L)*Z11 + AV(J)*CV(L)*Z22 +
1457        $                  AW(J)*CW(L)*Z33 +
1458        $                  (AV(J)*CW(L) + AW(J)*CV(L))*Z23 +
1459        $                  (AU(J)*CW(L) + AW(J)*CU(L))*Z13 +
1460        $                  (AU(J)*CV(L) + AV(J)*CU(L))*Z12
1461   C
1462   C
1463                    COS5 = TZEF/(TZA(J)*TZC(L))
1464                    IF(COS5.GE.1.0.OR.COS5.LE.-1.0) GO TO 540
1465                    TZBE = (ACOS(COS5))*RADIAN
1466                    IF((TOLI5-ABS(TZBE-YBE)).LT.0.0) GO TO 540
1467   C
1468   C               —— THIS COMBINATION OF THREE MATRIX TRIPLES
1469   C                  TRANSFORMS CELL Z TO CELL Y WITHIN
1470   C                  THE SPECIFIED TOLERANCES — ASSIGN
1471   C                  THE ELEMENTS TO THE MATRIX H
1472                    U1 = AU(J)
1473                    V1 = AV(J)
1474                    W1 = AW(J)
1475                    U2 = BU(K)
1476                    V2 = BV(K)
1477                    W2 = BW(K)
1478                    U3 = CU(L)
1479                    V3 = CV(L)
1480                    W3 = CW(L)
1481   C
1482   C               —— ASSIGN AND CALCULATE VALUES FOR
1483   C                  TOLERANCE MATRIX
1484                    TOLA = DA(J)
1485                    TOLB = DB(K)
1486                    TOLC = DC(L)
1487                    TOLAL = TZAL - YAL
1488                    TOLBE = TZBE - YBE
1489                    TOLGA = TZGA - YGA
1490   C
1491   C               —— CALCULATE INVERSE
1492                    UI1 =  (V2*W3 - V3*W2)/HDET
1493                    VI1 = -(V1*W3 - V3*W1)/HDET
1494                    WI1 =  (V1*W2 - V2*W1)/HDET
1495                    UI2 = -(U2*W3 - U3*W2)/HDET
1496                    VI2 =  (U1*W3 - U3*W1)/HDET
1497                    WI2 = -(U1*W2 - U2*W1)/HDET
1498                    UI3 =  (U2*V3 - U3*V2)/HDET
1499                    VI3 = -(U1*V3 - U3*V1)/HDET
1500                    WI3 =  (U1*V2 - U2*V1)/HDET
```

```
1501  C
1502  C                              ―― WRITE MATRIX AND INVERSE,
1503  C                                  TOLERANCES, DETERMINANT
1504                                  CALL OUTPT2(7)
1505  C
1506      540                      CONTINUE
1507      545            CONTINUE
1508  C
1509  C
1510      550            CONTINUE
1511      555    CONTINUE
1512  C
1513  C
1514      565 CONTINUE
1515  C
1516      900 CONTINUE
1517          RETURN
1518     6000 FORMAT(////1X,'*HMATRX* ERROR ... More than 2000 possible matrix r
1519         $ows have been generated.'/1X,19X,'Input parameters and/or program
1520         $array sizes must be changed.')
1521     9500 FORMAT(1X,'ICTMA =',I5,5X,'ICTMB =',I5,5X,'ICTMC =',I5//)
1522          END
```

Figure 5:
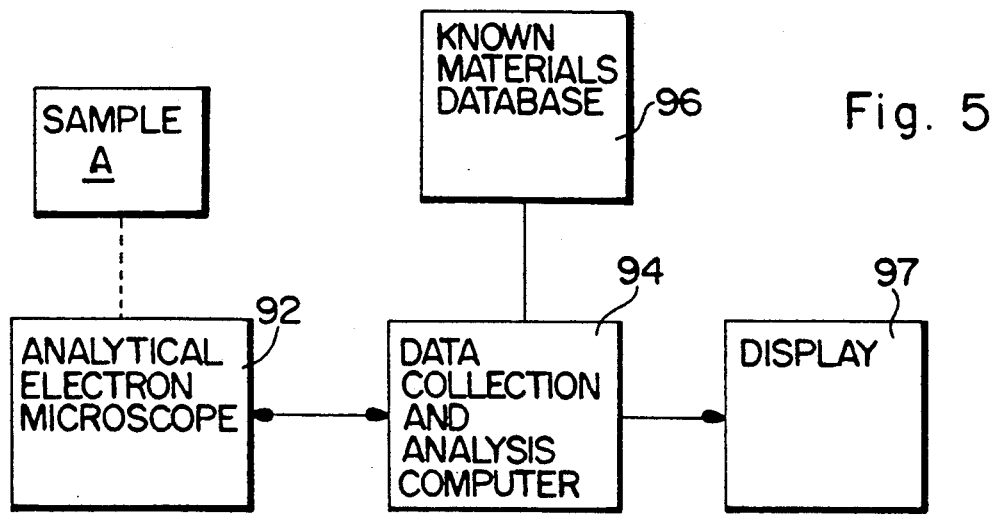
FIG. 5 is a block diagram of analytical electron microscope apparatus according to the present invention for identifying an unknown material.
Figure 6:
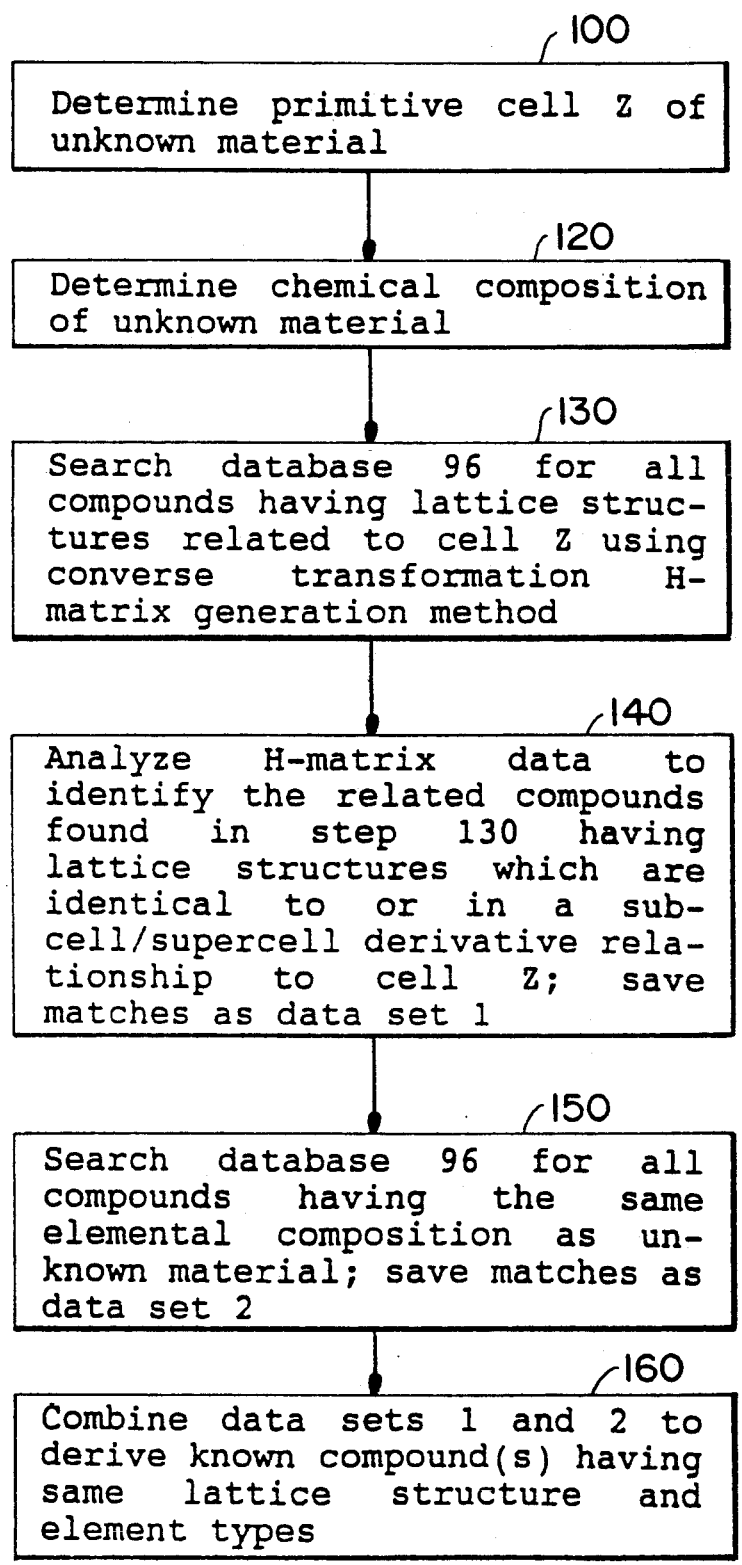
FIG. 6 is a flow chart of a preferred method of data collection and analysis performed by the apparatus of FIG. 5 according to the present invention.
Figure 7:
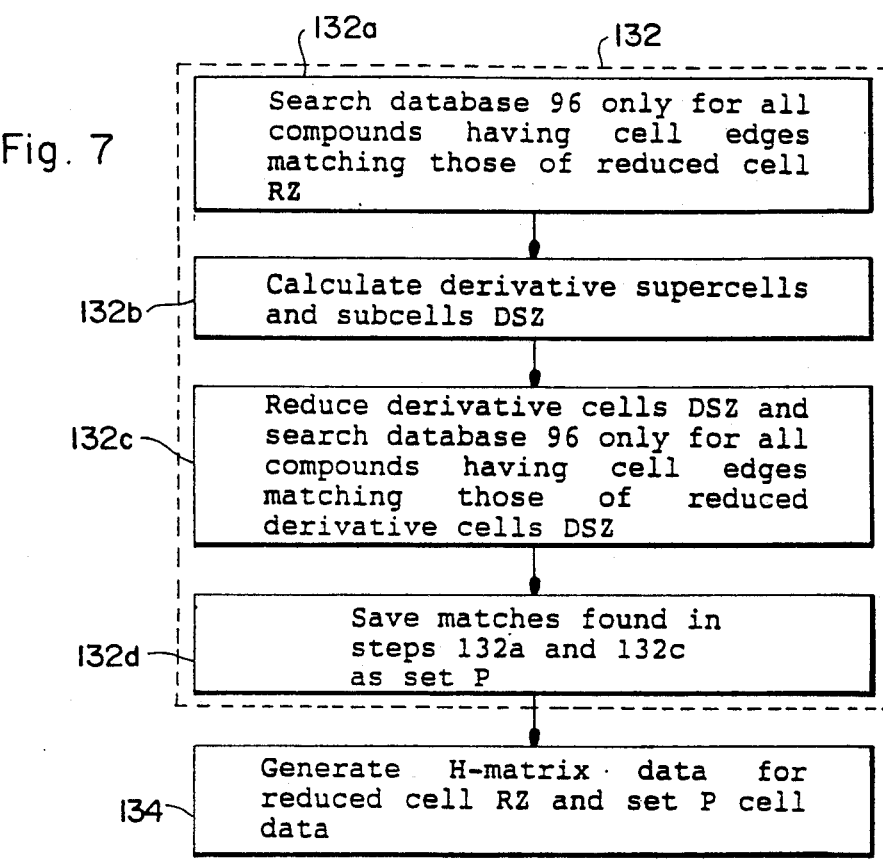
FIG. 7 is a more detailed flow chart of a preferred embodiment of step 130 in FIG. 6.

Referring to FIGS. 5-7, a method for phase identification of an unknown crystalline material utilizing the converse transformation method according to the present invention will now be described which is particularly suited for computer implementation and use with electron diffraction and energy dispersive x-ray spectroscopy data obtained from analytical electron microscopes (AEM) or single-crystal X-ray diffractometers, and the large databases on solid-state materials which have now been compiled.

Referring specifically to FIGS. 5 and 6 the first two steps are to determine (step 100) any primitive cell Z that characterizes the unknown lattice structure and to determine (step 120) the chemical composition of the unknown lattice structure. These two steps may be accomplished in any conventional manner, such as by using a conventional AEM 92. Preferably, primitive cell Z is determined in the manner described hereinabove with respect to step 10 of FIG. 2 using a sample A of the material under study. The chemistry of the unknown material is then determined using conventional techniques on precisely the same sample A used to determine primitive cell Z in step 10. Both the elements present as well as the elements absent in the sample are determined. This can be done efficiently using conventional energy dispersive x-ray spectroscopy (EDS) techniques. The sample cell and chemistry data is fed to a data analysis computer 94 which executes the following computations.

The next step (step 130) is to have computer 94 search a database 96 of materials with known lattice structures to find all compounds that have a lattice structure related to that of the unknown material. One suitable database is NIST CRYSTAL DATA, a large computer accessible database containing chemical, physical and crystallopgraphic data on approximately 140,000 solid-state materials, including all commonly occuring materials, which has been complied and evaluated by the NIST Crystal Data Center, United States National Institute of Standards and Technology. In the NIST CRYSTAL DATA database, the lattice structure of each material is represented by its standard reduced cell.

The converse transformation matrix generation method of the present invention advantageously is used by computer 94 to perform the lattice matching of step 130. However, in order to enhance the computer speed of the matching process, step 130 preferably comprises a first matching step 132 using a reduction technique as follows, followed by a second matching step 134 using the converse transformation matrix generation method. Referring specifcally to FIG. 7, it is assumed that the primitive cell determination of step 10 (FIG. 5) included reduction of the cell to provide a reduced cell RZ, and that the lattice data in database A is in the form of standard reduced cells, as is the case with the NIST CRYSTAL DATA database. The reduced cell RZ is first searched (step 132a) against database 96 for a match on cell edges but not cell angles. In step 132b, derivative supercells and subcells DSZ are calculated for cell RZ. In step 132c, derivative cells DSZ are reduced and searched against database 96 for a match of cell edges but not cell angles. Finally, in step 132d, the matches found in steps 132a and 132c are saved as a set P for further processing in step 134.

A computer program developed by applicants, NBS*SEARCH, which is publicly available from The National Institute of Standards and Technology, advantageously is used to carry out step 132. The NBS*SEARCH program is highly efficient because it uses a grouped-entry direct access search strategy, the underlying theory of which is described in applicants' publications: "NBS*SEARCH, A Program to Search NBS CRYSTAL DATA", Version of Spring, 1987, NBS Crystal Data Center, Nat'l Bur. of Standards; "NBS*LATTICE: A Program to Analyze Lattice Relationships," U.S. Nat'l Bur. Standards Tech. Note 1214 (1985), and "Compound Identification and Characterization using Lattice-Formula Matching Techniques", Acta Cryst. A42 (1986), pp. 101-105. Although the NBS*SEARCH program can be used to match on angles as well as edges, it is far more reliable to carry out a full lattice match using the converse transformation matrix procedure of the present invention.

It will be appreciated from the foregoing that use of the converse transformation matrix method of the present invention in step 134 following step 132 entails comparing both the edge and angle parameters of reduced cell RZ of the unknown material with the limited set P of possible matching lattices derived in step 132 by finding, for each of the known lattice cells Y in set P, all matrices H (if they exist) that relate cell RZ to the known lattice cell (Y) to within specified tolerances of the lattice parameters.

Next, in step 140 (FIG. 6), the H-matrix data generated in step 130 is analyzed to determine the relationship of the unknown material lattice structure to the known lattice structures determined to be matching lattice structures in step 130. The following relationships are readily ascertainable:

a) Unknown cell Z and a matching known cell Y define the same lattice structure if step 130 finds a matrix H with integer elements U1–U3, V1–V3, and W1–W3 and a determinant HDET=1 that will transform cell Z to cell Y. If both cells Y and Z are reduced, then only the following values for each matrix element need to be considered: −1, 0, and 1.

b) Unknown cell Z and a matching known cell Y define lattice structures that are in a derivative subcell or supercell relationship if step 130 finds a matrix H such that either i) the matrix H has integer elements, a determinant HDET>1 and will transform cell Z to cell Y; or ii) its inverse matrix H' has integer elements, a determinant HDET>1, and will transform cell Y to cell Z. A typical range of matrix elements in such a case includes the integer and non-integer reciprocals thereof in the range ±6, i.e., −6, −5, −4, −3, −2, −1, −$\frac{1}{2}$, −$\frac{1}{3}$, −$\frac{1}{4}$, −1/5 0, 1/5, $\frac{1}{4}$, $\frac{1}{3}$, $\frac{1}{2}$, 1, 2, 3, 4, 5, 6.

c) Unknown cell Z and matching known cell Y define lattice structures that are in a composite relationship if step 130 finds a matrix H such that i) the matrix H has one or more fractional elements and will transform cell Z to cell Y; and ii) its matrix inverse H' also has one or more fractional elements and will transform cell Y to cell Z. A typical range of matrix elements in such a case includes the integers and non-integer reciprocals thereof in the range ±6, i.e., −6, −5, −4, −3, −2, −1, −$\frac{1}{2}$, −$\frac{1}{3}$, −$\frac{1}{4}$, −1/5, 0, 1/5, $\frac{1}{4}$, $\frac{1}{3}$, $\frac{1}{2}$, 1, 2, 3, 4, 5 and 6.

It will be appreciated that in most phase characterization studies, only the first two relationships described above are of interest. Routinely checking for sub/super-lattice relationships is particularly useful in that it permits identification despite certain categories of experimental errors. The known lattices cells Z determined to have either the same or a sub- or super-cell relationship to unknown cell Y are thus advantageously stored as a first data set 1.

In the next step 150, database 96 is searched to determine all known compounds with the same elemental composition as the unknown material. The results of the search are saved in a second data set 2. With the NIST CRYSTAL DATA database, this is a straightforward operation, since the database contains an empirical formula with the elements in alphabetical order for each material. Preferably, the element search is set to find all database compounds that have precisely the same elements as the unknown *and* no other elements. In this type of search, knowledge of the elements not present allows the database to be screened to usually obtain a highly limited set of potential matches.

Finally, in step 160, the unknown material is identified by analyzing the results of steps 140 and 150. Advantageously, this is done simply by logically combining the data sets 1 and 2 using the Boolean AND operation to form a third data set 3 containing the data entries which are present in both sets 1 and 2. Hence, the entries in data set 3 have the same lattice structure and element types as the unknown material. Since research work has shown that materials can be accurately characterized on the basis of their lattice structures and chemical composition, it can be reasonably assumed that if an unknown material has the same lattice structure and "element types" as a known material in database A, the unknown material is the same compound.

Figure 8:
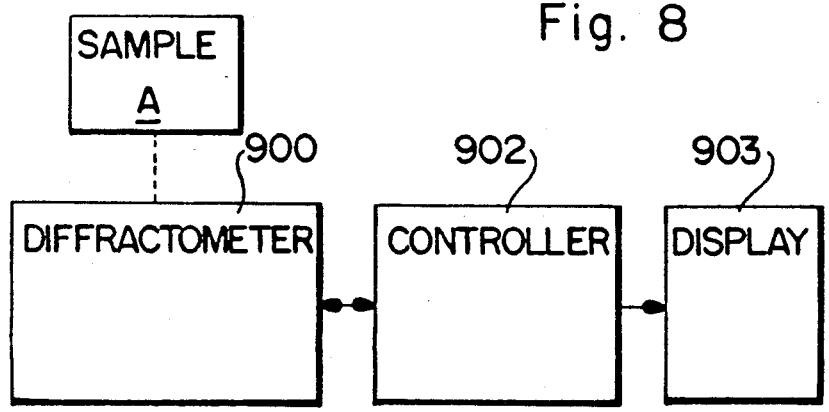
FIG. 8 is a block diagram of automated diffractometry apparatus according to the present invention for symmetry analysis of a lattice structure.
Figure 9:
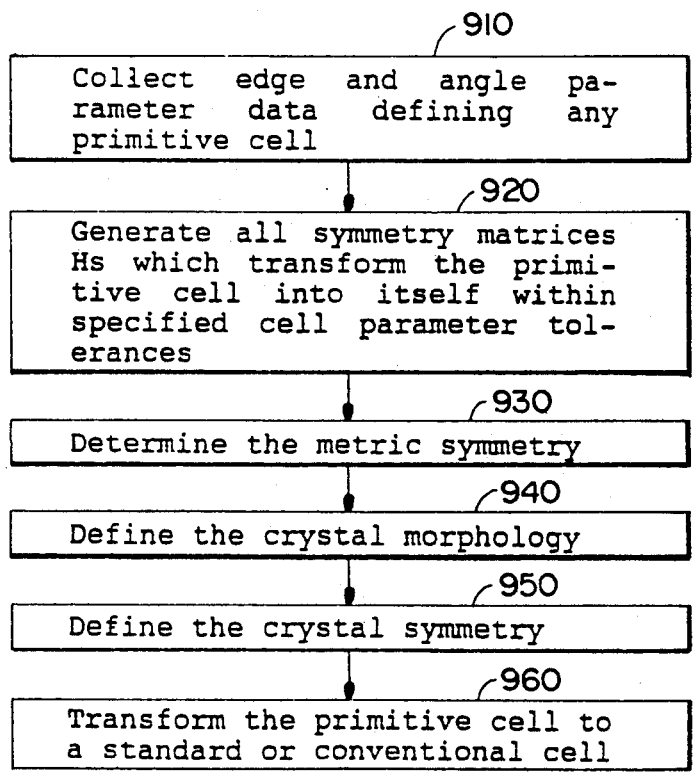
FIG. 9 is a flow chart of a preferred method of data collection and analysis performed by the apparatus of FIG. 8.

The use of the converse transformation matrix generation method of the present invention in conjunction with symmetry analysis of lattice structures by an automated diffractometer will now be described. Referring to FIG. 8, an automated diffractometer according to the present invention comprises a conventional diffractometer 900 which includes a microprocessor-based controller 902 for controlling the orientation of a sample A relative to the diffractometer, and detecting and analyzing the diffraction signal data produced by the diffractometer. Referring to FIG. 9, the analysis of lattice symmetry according to the present invention is accomplished by collecting edge and angle parameter data with diffractometer 900 (step 910); defining any primitive cell and using the converse transformation matrix generation method of the present invention described hereinabove to generate a set (or sets) of symmetry matrices Hs which transforms the primitive cell into itself (step 920). More specifically, the symmetry matrices Hs in the following equation are determined:

$$a_i = \sum_j H_{sij} a_j \ (i, j = 1, 2, 3),$$

where $a_i$ and $a_j$ define two primitive triplets of noncoplanar translations. Only matrices Hs with integer elements and a determinant HDET of +1 are considered. The primitive cell advantageously is defined as described hereinabove in connection with step 10 of FIG. 2. It will be appreciated that the data collection can be carried out by diffractometer 900 with respect to any basis.

The next step (930) is to determine the metric symmetry, which is accomplished through analysis of the tolerance matrices generated with the matrices Hs produced in step 920, and to assess the experimental error of unit cell parameters (which errors are directly related to the refined cell parameters). As discussed hereinabove, generated with each symmetry matrix Hs is a tolerance matrix T, which represents the tolerances (either absolute or relative percentage tolerances) in the cell parameters required to transform the primitive cell into itself by the specified matrix Hs. If the converse transformation method of the present invention generates a symmetry matrix Hs having a tolerance matrix:

| tol a | tol b | tol c |
|-------|-------|-------|
| tol α | tol β | tol γ | then the transformation of a first cell by the matrix Hs will produce a second cell having the parameters

| | | |
|---|---|---|
| a' = a + tol a | b' = b + tol b | c' = c + tol c |
| α' = α + tol α | β' = β + tol β | γ' = γ + tol γ |

Thus the matrix method of the present invention enables a direct comparison of the calculated errors with the experimental errors for the refined unit cell. Further, by initially assuming very large experimental errors, a menu of all possible symmetries can be obtained from which the highest possible metric symmetry can be determined.

By analyzing the symmetry matrices Hs and associated tolerance matrices T, the metric symmetry groups are defined. The tolerance matrices T for the group(s) of symmetry matrices indicate precisely how the initially selected primitive cell deviates from exact metric symmetry and pseudosymmetry. In theory, it is the nature of the matrices themselves that defines the sets to be analyzed (i.e., those defining a symmetry group). In practice, however, the usual result is that the tolerance matrices alone clearly define the groups. Thus, with this approach, all possible symmetries and pseudosymmetries to within any specified maximum acceptable tolerance are immediately apparent. After a group of symmetry matrices Hs has been determined, the metric symmetry is deduced simply by counting the number of matrices in the group. The greater is the number of matrices, the higher is the symmetry. For example, the numbers of matrices for the seven lattice metric symmetries are: anorthic (triclinic): one; monoclinic: two; orthorhombic: four; rhombohedral: six; tetragonal: eight; hexagonal: twelve; and cubic: twenty-four.

When the symmetry matrices are used to transform an experimentally determined unit cell, metrically similar unit cells are generated. If the lattice symmetry elements correspond to crystallographic symmetry elements, then these metrically similar cells are symmetrically equivalent and the observed metric differences are due to experimental errors. The matrix approach to symmetry provides an ideal way to evaluate the experimental errors simply by averaging the set of tolerance matrices. The resulting "error" matrix (i.e., the averaged tolerance matrix) may be compared directly to the e.s.d.'s for the refined unit cell, or it may be applied to the refined unit cell to calculate an idealized cell reflecting the exact metric symmetry. In either case, the extent to which the refined cell parameters deviate from exact metric symmetry is easily established.

In step 940 the crystal morphology is defined by establishing the crystal size and faces for the primitive cell (basis) defined in step 910. This step permits absorption corrections to be applied, if necessary, as data is collected in connection with step 950, to permit the experimental symmetry and conventional cell to be defined.

In step 950, the crystal symmetry are defined, which entails using the symmetry matrices Hs to generate equivalent intensities (h. k. l)$_{eq}$ from the collected diffraction intensity data (h,k,l) using the equation:

$$\left[\begin{pmatrix} h \\ k \\ l \end{pmatrix}_{eq}\right]_i = Hi \begin{pmatrix} h \\ k \\ l \end{pmatrix}$$

Next, if necessary, absorption corrections are calculated in step 954 from the morphology data derived in step 940, and the corrections are applied to the equivalent intensities to facilitate comparison thereof. In step 956, the Laue symmetry is established using the equivalent intensities (h,k,l)$_{eq}$ derived in step 952 (954), which the present invention permits to be done without risk of assigning a Laue group of too low a symmetry. In certain cases the intensity measurements will prove that the Laue symmetry is less than that predicted from the metric lattice symmetry. That is, the intensities of all the potentially equivalent (h,k,l)'s are not equal. In these cases, group-subgroup relationships and structural pseudosymmetry can be determined by evaluating the nature of the symmetry matrices in conjunction with the intensity data.

Unlike other methods, the matrix approach of the present invention permits the collection of experimental data and the assignment of the Laue symmetry with respect to any basis. Mistakes in the Laue symmetry are avoided since it is not necessary to do key experimental steps out of order. In the matrix approach, all the data required to assign the Laue symmetry are collected before a conventional cell is determined. In contrast, procedures currently used in diffractometry are based on the risky practice of assuming a conventional cell and symmetry, and then collecting data to verify the assumption. This erroneous strategy may lead to the assignment of a Laue group of too low symmetry.

The next step (958) in defining the crystal symmetry is to calculate the nature and directions of the symmetry axes. Since the values of the elements in each symmetry matrix Hs depend upon the kind and orientation of the element with respect to the coordinate system chosen, the symmetry matrices themselves can be analyzed to define both the nature and directions of all symmetry operations of the lattice. The nature of the symmetry axis is found by calculating the trace of the matrix: $tr(H) = H_{11} + H_{22} + H_{33}$. The trace of the matrix is invariant under the similarity transformation, i.e., it is independent of the basis chosen. The symmetry axis is an n-fold rotation axis wherein n=1, 2, 3, 4, 6 for $tr(H) = 3, -1, 0, 1, 2$, respectively. Depending on the application, the direction of each axis is given by the solutions q of a linear algebraic equation of the form $(H-1)q=0$, which is the lattice approach, or $((H^{-1})^t - 1)q = 0$, which is the object approach, where 1 is the identity matrix. The final step 959 in defining the crystal symmetry is to control diffractometer 900 using the symmetry axis data from step 958 to obtain sample orientations for photographs of symmetry in planes of reciprocal space for desired symmetry axes of the primitive cell. As the matrix approach of the present invention enables *all* symmetry axes to be identified without transformation to standard orientations, *all* symmetry axes in reciprocal space can be identified once *any* cell has been determined for an unknown material.

The final step (960) in the diffractometer control method of the present invention is to transform the primitive cell to a standard or conventional cell. In a first embodiment of step 960 (FIG. 11), an idealized cell is calculated (step 962) by analyzing the cell parameter errors determined in step 930. The idealized cell is then reduced (step 964), and then the *International Tables for Crystallography*, Vol. A, published for the International Union of Crystallography by D. Reidel Publishing Comp. (1983), pages 734–735, are searched (step 966) to find a transformation matrix to a conventional cell. This embodiment has the advantage of eliminating all interactions of the cell parameter errors with the reduction calculations. In a second embodiment of step 960, the nature and directions of the symmetry axes with respect to the original basis for any primitive cell which were experimentally determined in step 958 are also used to obtain a transformation matrix to a standard, conventional, or even a second skewed cell. When choosing a conventional cell, any required metric constraints may be applied separately. A set of conventions used for choosing cell edges based on symmetry, plus additional metric constraints when necessary, are given in the aforementioned *International Tables For Crystallography*.

Two conceptually different approaches may be used to analyze the group of symmetry matrices and to derive a standard cell transformation matrix: the lattice approach and the object approach. Either strategy is ideal for diffractometry. In addition, the choice of directions to be used as cell edges advantageously can be made either through analysis of dependency equations or analysis of determinants. In obtaining a suitable transformation matrix, calculations are carried out with full knowledge of the crystal system and the nature and directions of the symmetry axes. Thus, a transformation matrix to a basis which is most convenient for the study that is being carried out can always be obtained.

Figure 12:
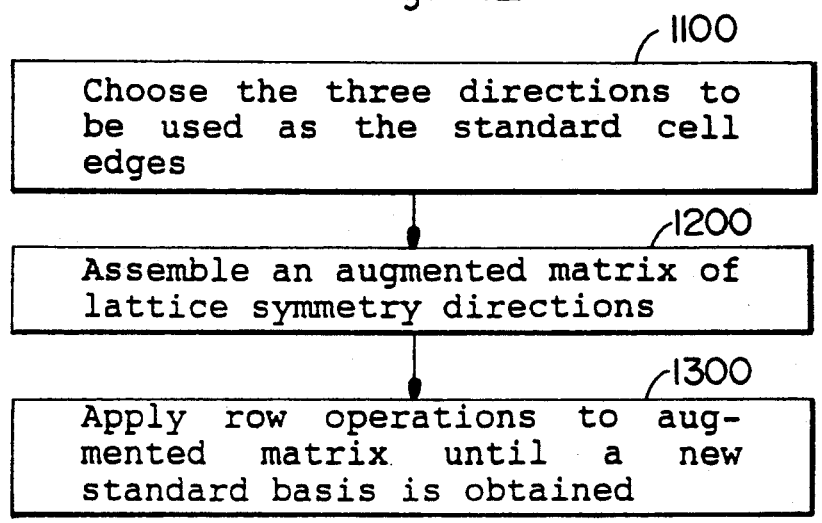
FIG. 12 is a more detailed flow chart of a second embodiment of step 960 in FIG. 9.

The lattice approach (FIG. 12) obtains a transformation matrix from a skewed cell to a standard cell by analyzing the symmetry of the lattice. Each symmetry matrix Hs is used directly to calculate the nature of the symmetry axis and the direction of the axis with respect to the lattice. After the proper three directions for the standard cell edges have been chosen (step 1100) as described hereinbelow, the task of obtaining a transformation matrix becomes a change-of-basis problem in linear algebra. That is, a skewed basis is to be transformed into a new standard basis. The first step (step 1200) in solving this change of basis problem is to assemble an augmented matrix of lattice symmetry directions, where the directions are written as columns. The three symmetry directions chosen for the cell edges will be the first three columns in the augmented matrix and should be assembled with account taken of certain crystallograhic conventions. These include the definition of a riqht-handed coordinate system and observation of the preferred order of the axes. As summarized below, a transformation matrix from a skewed to a standard cell is found by applying elementary row operations to the augmented matrix until a new standard basis is obtained (step 1300)

$$\left( \text{skewed basis} \left| \begin{array}{c} \text{symmetry} \\ \text{directions} \\ \text{(optional)} \end{array} \right| \begin{array}{c} 100 \\ 010 \\ 001 \end{array} \right) \rightarrow$$

$$\left( \text{new basis} \left| \begin{array}{c} \text{symmetry} \\ \text{directions} \\ \text{(new basis)} \end{array} \right| \text{transformation matrix} \right)$$

The new basis can be any 3×3 matrix. However, when determining a transformation matrix to a conventional unit cell, the new basis is usually the identity matrix and the mathematical operation involved is simply the taking of the inverse of a 3×3 matrix by reducing an augmented matrix to row echelon form. The choice of basis influences the relationships between the remaining vectors as well as the interpretation of the last three columns to give a transformation matrix. This is especially true for centered lattices and for the rhombohedral system. Although many variations are possible owing to the many bases that can be chosen, the relationships between the vectors is well defined and, in practice, the determination of a transformation matrix is straightforward for all cases. The lattice approach may be viewed as one form of lattice or cell reduction based on symmetry.

Figure 13:
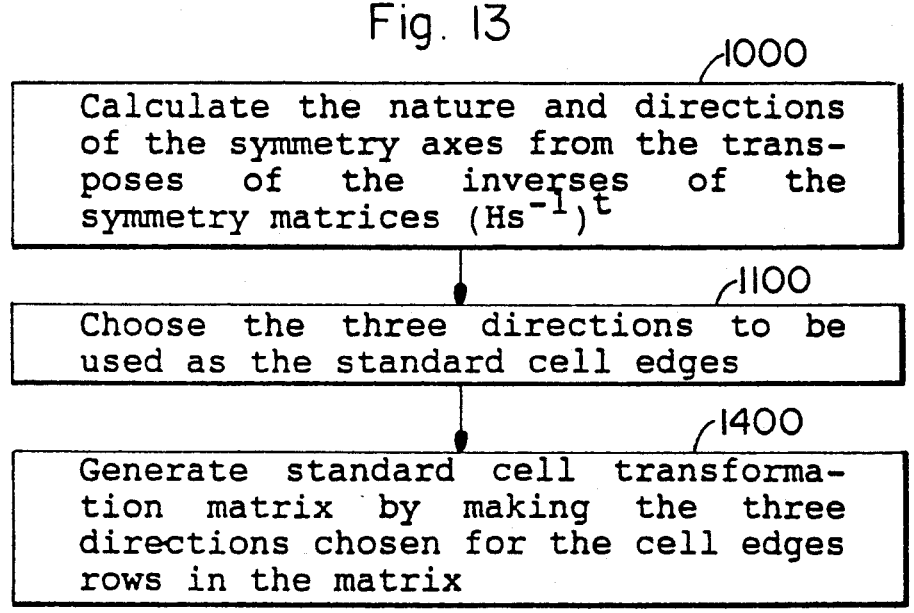
FIG. 13 is a more detailed flow chart of a third embodiment of step 960 in FIG. 9.

Because the symmetry matrices are generated by relating a cell to itself, the symmetry operations of the lattice are obtained. However, symmetry is often described in terms of equivalent positions for objects. This is the basis used for the object approach (FIG. 13). As explained hereinabove with respect to Laue symmetry, the matrices Hs may be viewed as matrix representations of equivalent (h,k,l)'s. Therefore, in order to shift the emphasis from lattices or intensities (h,k,l)'s to objects or (x,y,z)'s, the nature and directions of the symmetry axes are calculated (step 1000) from the transposes of the inverses of the symmetry matrices, $(Hs^{-1})^t$, and the three directions for the cell edges are chosen (step 1100) as described hereinbelow. With this approach, the task of obtaining a transformation matrix is greatly simplified because the standard basis is the identity matrix and the standard matrix for a matrix transformation is the matrix itself. This means that the transformation matrix from any skewed cell to a conventional cell is obtained directly by making the three directions chosen for the cell edges rows in a matrix (step 1400). As in the case of the lattice approach, the transformation matrix should be assembled so that the crystallographic conventions are met. The type of centering present is defined by a value for the determinant of the transformation matrix, except in orthorhombic systems where additional information is sometimes required.

Whether the lattice or the object approach is used to determine a transformation matrix to a standard cell, an important step is the selection of three linearly independent vectors in the proper directions to be used as directions for the cell edges (step 1100). In the triclinic system, selection of cell edges is based on metric conditions. In the monoclinic system, the only symmetry direction, a two-fold axis, is labelled as b (the vectors a and c are chosen so that they lie in a plane perpendicular to b and meet additional metric constraints). The directions of the three two-fold axes in the orthorhombic system are selected for the cell edges. In the rhombohedral system, the directions for any two of the three two-fold axes and the direction of a three-fold axis are used as directions for a, b, and c, respectively. The resulting transformation may give either metrically rhomohedral or metrically hexagonal axes depending on the relationships between these vectors, i.e., the basis chosen. In the tetragonal system, the directions for two of five possible two-fold axes are taken as the a and b axes while the direction of a four-fold axis is selected for the c axis. Similarly, in the hexagonal system, directions for two of the seven two-fold axes are selected for a and b and the direction of a six-fold axis is selected for c. The cell edges for the cubic system are taken along three linearly independent four-fold axes. Thus, when choosing three symmetry directions to be used as cell edges, only the tetragonal and hexagonal crystal systems appear to allow more than one possibility.

Figure 14:
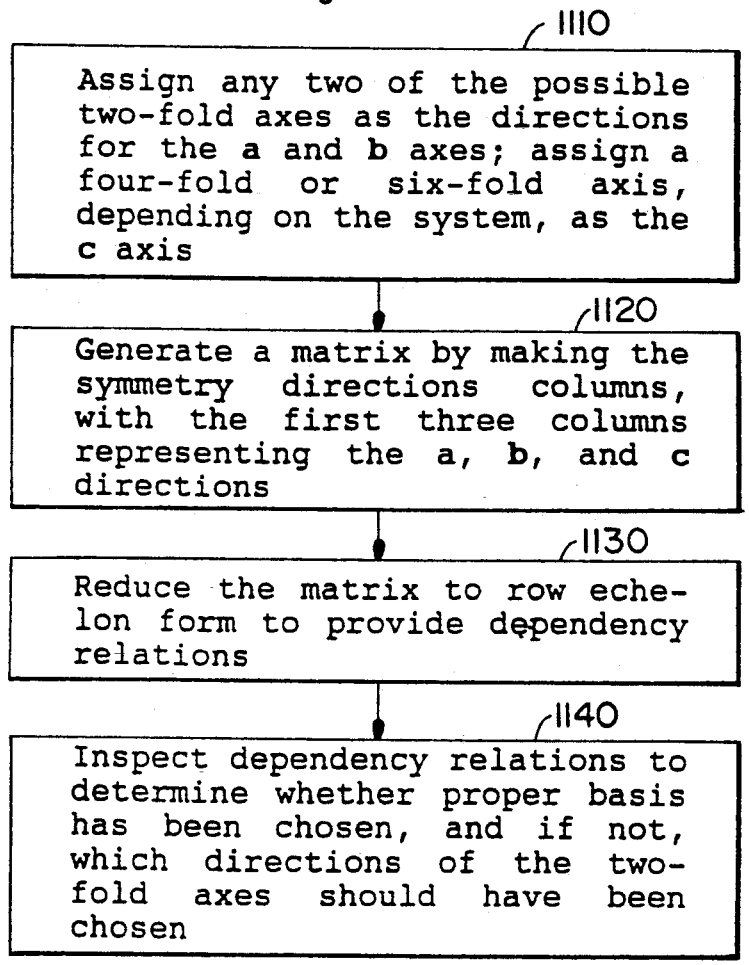
FIG. 14 is a more detailed flow chart of a first embodiment of step 1100 in FIGS. 12 and 13.

The analysis-of-dependency-equations approach to choosing the directions to be used as cell edges will now be described with reference to FIG. 14. In the tetragonal system, five of the matrices correspond to two-fold axes. Since one of these five axes is parallel to a four-fold axis, there are at most six combinations of two-fold axes to be considered. Likewise, in the hexagonal system, one of seven two-fold axes is parallel to a six-fold axis, leading to at most fifteen ways to choose two of the remaining six directions.

The first step (step 1110) in the dependency equation procedure is to pick any two of the possible two-fold axes and arbitrarily assign these as the directions for the a and b axes. The direction used for the c axis is that of a four-fold axis in the tetragonal system and a six-fold axis for the hexagonal system. Next (step 1120), a matrix is generated by making the symmetry directions columns, with the first three columns representing the a, b, and c directions. Using elementary row operations, the matrix is then reduced (step 1130) to row echelon form. This step gives the dependency equations for the remaining symmetry directions with respect to the basis directions chosen.

Simply by inspecting the dependency relations obtained from the reduced row echelon form of the matrix, it can be determined whether a proper basis has been selected and, if not, which directions of the two-fold axes should have been chosen (step 1140). Each of the six combinations of the two-fold axes in the tetragonal system leads to one of three recognizable types of matrices. Similarly, in the hexagonal system, each of the fifteen combinations of two-fold axes falls into one of four recognizable forms of matrices. When the reduced row echelon form of the matrix for the tetragonal or the hexagonal system is order of axis $$\begin{matrix} 2 & 2 & 4 & 2 & 2 \\ \end{matrix}$$
$$\begin{pmatrix} 1 & 0 & 0 & 1 & 1 \\ 0 & 1 & 0 & -1 & 1 \\ 0 & 0 & 1 & 0 & 0 \end{pmatrix}$$

or order of axis $$\begin{matrix} 2 & 2 & 6 & 2 & 2 & 2 \\ \end{matrix}$$
$$\begin{pmatrix} 1 & 0 & 0 & 1 & -1 & 1 & -2 \\ 0 & 1 & 0 & -1 & -1 & 2 & -1 \\ 0 & 0 & 1 & 0 & 0 & 0 & 0 \end{pmatrix}$$

respectively, or its equivalent, the proper basis has been chosen.

Perhaps the easiest way to understand the dependency equations in the reduced row echelon form of the matrix is through use of a diagram. For both the tetragonal and hexagonal systems, the vectors projected onto the ab plane are plotted and the respective figures are compared with those for space groups P4/mmm and P6/mmm in *International Tables For Crystallography* (1983). With a plot of the dependency equations, the vectors that have been chosen, and if necessary, which vectors should have been selected, can be readily visualized.

The analysis-of-dependency-equations method for selecting the directions of symmetry axes to be used as cell edges is similar in approach to the lattice method of obtaining a standard cell transformation matrix, as both methods use elementary row operations to reduce a matrix to a row echelon form. The lattice method may be viewed as a form of lattice reduction, whereas the analysis-of-dependency-equations method may be viewed as a form of symmetry reduction.

Figure 15:
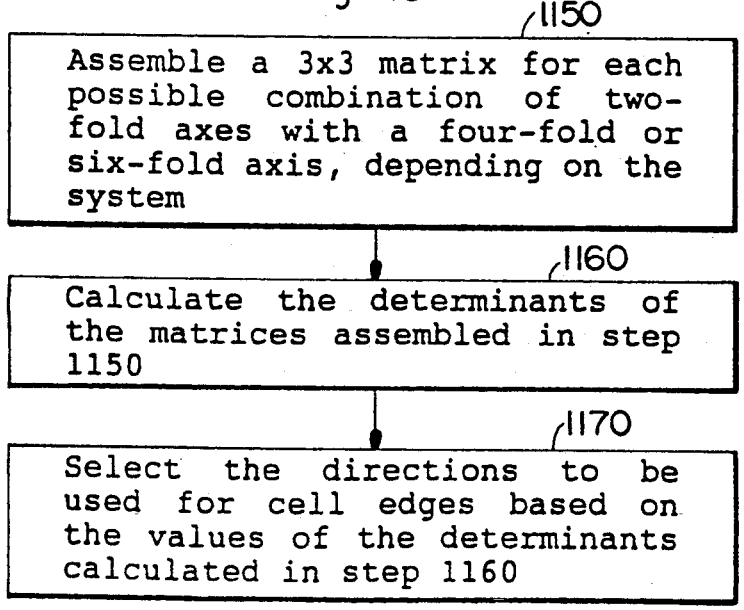
FIG. 15 is a more detailed flow chart of a second embodiment of step 1100 in FIGS. 12 and 13.

The determinant method (FIG. 15) for selecting the directions of symmetry axes to be used as cell edges greatly simplifies the analysis based on symmetry because data is analyzed with respect to any orientation without having to view it, either visually or mathematically, from a standard basis. In the tetragonal system, there are six ways to combine two two-fold axes with a four-fold axis. Similarly, in the hexagonal system, there are fifteen ways to combine two two-fold axes with a six-fold axis. For each combination, a 3×3 matrix of directions is assembled (step 1150). The determinants of these matrices are then calculated (step 1160). The directions to be used for the cell edges are found directly from the values of the determinants of these matrices (step 1170). In the tetragonal system, one of the six determinants will be twice the others. If the four possible two-fold axes are labelled 1, 2, 3, and 4, the combination of 1 and 2 with a four-fold axis gives a determinant twice the rest, and the vectors 3 and 4 should be selected as directions for the conventional cell edges. As another example, in the hexagonal system, there will be nine combinations with a determinant of ±1, three combinations with a determinant of ±2, and three combinations with a determinant of ±3. If the six possible two-fold axes are labelled 1-6, and the combinations of 1-2, 1-3, and 2-3 give determinants of ±3, then the directions for any two of the two-fold axes 4, 5 or 6 may be used as cell edges.

Often in carrying out practical or theoretical calculations in which symmetry is involved, it is convenient to shift basis systems. The matrix approach of the present invention permits groups of symmetry matrices to be obtained with respect to any selected basis. The values of the elements in each symmetry matrix depend on the kind and orientation of each symmetry operation with respect to the coordinate system chosen. As a result, the group of symmetry matrices generated from a skewed unit cell will be different from the group symmetry matrices generated from either a standard cell or a second skewed cell. Since any two cells defining the lattice belong to the same Bravais class, there exists a homogeneous linear transformation which will transform one lattice into the other and will transform the holohedry of one lattice into the holohedry of the other. The matrices may be calculated either directly using the reverse transformation method of the present invention; or by application of the similarity relationship, once the matrices are known with respect to any initial basis. The transformation of cell 1 to cell 2 is represented by the equation $$\begin{pmatrix} a_2 \\ b_2 \\ c_2 \end{pmatrix} = S \begin{pmatrix} a_1 \\ b_1 \\ c_1 \end{pmatrix}$$

and the holohedry of cells 1 and 2 is defined by $\{H_1\}$ and $\{H_2\}$, respectively, where $H_1$ and $H_2$ are groups of symmetry matrices Hs. The relationship between the symmetry groups $H_1$ and $H_2$ is given by the equation $H_2 = SH_1S^{-1}$. This equation defines the effect a change of basis has on the matrix of a linear operator. By definition, two matrices representing the same linear operator with respect to different bases are similar.

While the present invention has been described with reference to a particular preferred embodiment of the method and apparatus, the invention is not limited to the specific example given, and other embodiments will be apparent to those skilled in the art without departing from the spirit and scope of the invention.

What is claimed is:

1. Automatic apparatus for identifying an unknown crystalline material comprising:
   a radiation generator for irridating a sample of the unknown material with radiation;
   a radiation detector for detecting radiation received from the irridated sample and producing electrical output signals indicative of the detected radiation;
   an electronic signal analyzer, responsive to said electrical output signals generated by said radiation detector, for producing electrical data signal outputs indicative of a primitive lattice cell Z of the unknown material, said cell Z having three cell edges ZA, AB and ZC, respectively, and three cell angles ZAL, ZBE, and ZGA, respectively;
   a first computer accessible memory in which is stored a database comprising lattice cell data for materials with known lattice structures;
   first computer search means responsive to said electronic signal analyzer data signal outputs for automatically searching said database using a converse transformation method to generate matrices H identifying all materials, if any, having lattice cell structures related to cell Z; and
   computer means for analyzing any matrices H generated by said first search means to identify which of the database materials identified by the generated matrices H match cell Z by having a lattice cell structure identical to or in a subcell/supercell derivative relationship to cell Z, any database material so identified as matching cell Z constituting a possible identification of the unknown crystalline material.

2. The apparatus of claim 1 wherein a diffractometer constitutes said radiation generator and radiation detector.

3. The apparatus of claim 2 wherein said diffractometer is selected from the group consisting of an x-ray diffractometer which irradiates the sample of the unknown material with x-ray radiation, an electron diffractometer which irradiates the sample of the unknown material with electron radiation, and a neutron diffractometer which irradiates the sample of the unknown material with neutron radiation.

4. The apparatus of claim 2 wherein said signal analyzer further comprises a controller for controlling the orientation of the sample relative to said diffractometer.

5. The apparatus of claim 1 wherein an analytical electron microscope constitutes said radiation generator and radiation detector.

6. The apparatus of claim 1 wherein the materials with known lattice structures have chemical compositions, and said database further comprises element type data identifying the chemical compositions of the materials with known lattice structure, and said apparatus further comprises:
   means for determining the element types identifying the chemical composition of the unknown material and producing electrical signal outputs indicative of the unknown material element types;
   second computer search means responsive to the electrical signal outputs produced by said element type determining means for automatically searching said database for all compounds which match the unknown material by having the same or related element types as the unknown material;
   a computer accessible second memory for saving as a first data set the compounds matching cell Z identified by said matrix H analyzing means, and as a second data set the matching compounds with the same element types as the unknown material identified by said second search means; and
   said computer means includes means for combining said first and second data stored in said electronic memory to derive all known compounds having the same lattice cell structure and element types as the unknown material.

7. The apparatus of claim 6 wherein said means for determining element types comprises an energy dispersive x-ray spectrometer.

8. The apparatus of claim 1 wherein said first computer search means and said computer analyzing means cooperate to:
   search said database without generating said matrices H to identify all compounds which match said cell Z with respect to cell edges;
   determine derivative subcells and supercells of said cell Z;
   search said database without generating said matrices H to identify all compounds which match said derivative subcells or supercells with respect to cell edges; and
   search the compounds identified by said database searching using said converse transformation method to generate matrices H identifying those compounds which match cell Z with respect to both cell edges and cell angles.

9. The apparatus of claim 8 wherein:
   the lattice cell data in said database is in the form of reduced cell data;
   a reduced form of said cell Z is generated; and
   the derivative subcells and supercells are produced in reduced form.

10. The apparatus of claim 1 wherein said converse transformation method comprises the steps of:
   a) defining maximum acceptable cell edge and angle tolerances TOLI1, TOLI1, TOLI3 and TOLI4, TOLI5, TOLI6 for cell edges ZA AB and AC and cell angles ZAL, ZBE and ZGA, respectively, for the transformation of cell Z into another cell;
   b) finding all matrix triples AU, AV, AW; BU, BV, BW; CU, CV, CW which accomplish transformation, within the corresponding ones of said maximum cell edge tolerances TOLI1, TOLI2 and TOLI3, of the respective Z-cell edges ZA, ZB, and ZC to corresponding edges of a database cell;
   c) finding all combinations of said matrix triples found in said matrix-triple-finding step b) which accomplish transformation of the respective Z-cell angles to the corresponding angles of a database cell within the corresponding ones of said maximum acceptable cell angle tolerances TOLI4, TOLI5 and TOLI6.

11. The apparatus of claim 10 wherein said matrix triple finding step b) comprises the steps of:
b1) defining a set of possible matrix H elements HEL(JJ), HEL(KK), HEL(LL), where JJ, KK, and LL range from one to a predetermined number NHEL;
b2) deriving dot products Z11, Z22, Z33, Z23, Z13 and Z12 for cell Z as follows:

$$Z11 = ZA*ZA$$

$$Z22 = ZB*ZB$$

$$Z33 = ZC*ZC$$

$$Z23 = ZB*ZC*cos(ZAL/RADIAN)$$

$$Z13 = ZA/ZC*cos(ZBE/RADIAN)$$

$$Z12 = ZA*ZB*cos(ZGA/RADIAN)$$

$$RADIAN = 360/2\pi;$$

for each combination of HEL(JJ) HEL(KK) HEL(LL):
b3) determining a symmetrical dot product TZE for transformed cell Z, where $TZEE = HEL(JJ)*HEL(JJ)*Z11 + HEL(KK)*HEL(KK)*Z22 + HEL(LL)*HEL(LL)*Z33 + 2.0(HEL(KK)*HEL(LL)*Z23 + HEL(JJ)*HEL(LL)*Z13 + HEL(JJ)*HEL(KK)*Z12)$;
b4) determining whether TZEE is greater than zero, and if so, deriving a transformed Z-cell edge $TZEDG = \sqrt{TZEE}$; and
b5) determining whether TZEDG is a transformation, within said respective tolerances TOLI1, TOLI2, and TOLI3, of any of Z-cell edges ZA, ZB, ZC, to a corresponding one of the edges of the cell for a selected one of the materials in said database; and if so, saving the HEL combination as a matrix triple AU, AV, AW; BU, BV, BW; and/or CU, CV, CW, and saving a value TZA, TAB, and/or TZC=TZEDG, according to which edge(s) is (are) determined to be transformed.

12. The apparatus of claim 10 wherein said matrix triple combination finding step c) comprises the further steps of:
for each pair of matrix triples Au, Av, AW and BU, BV, BW:
c1) deriving a gamma value cos6 for a transformed cell TZ;
c2) determining whether gamma value cos6 is greater than or equal to +1 or less than or equal to −1, and if not, converting gamma value cos6 to an angle value TZGA;
c3) determining whether TZGA is within said maximum allowable tolerance TOLI6, and if so, for each matrix triple CU, CV, CW:
c4) deriving the determinant HDET of a transformation matrix defined by the combination of matrix triples AU, AV, AW; BU, BV, BW and CU, CV, CW;
c5) determining whether HDET is greater than zero, and if so, deriving an alpha value cos4 for said transformed cell TZ;
c6) determining whether alpha value cos4 is greater than or equal to +1 or less than or equal to −1, and if not, converting alpha value cos4 to an angle value TZAL;
c7) determining whether TZAL is within said maximum allowable tolerance TOLI4, and if so, deriving a beta value cos5 for said transformed cell TZ;
c8) determining whether beta value cos5 is greater than or equal to +1 or less than or equal to −1, and if not, converting beta value cos5 to an angle value TZBE;
c9) determining whether TZBE is within said maximum allowable tolerance TOLI4, and if so, saving the combination of matrix triples AU, AV, AW and BU, BV, BW as the elements U1, V1, W1, U2, V2, W2, U3, V3 and W3, respectively, of a transformation matrix H.

13. The apparatus of claim 12 wherein said gamma value cos6 deriving step comprises the steps of:
determining a value $TZEF1 = AU(J)*BU(K)*Z11 + AV(J)*BV(K)*Z22 + AW(J)*BW(K)*Z33 + (AV(J)*BW(K) + AW(J)*BV(K))*Z23 + (AU(J)*BW(K) + AW(J)*BU(K))*Z13 + (AU(J)*BV(K) + AV(AV(J)*BU(K))*Z12$; and
deriving gamma value $cos6 = TZEF1/(TZA(J)*TZB(K))$.

14. The apparatus of claim 12 wherein said alpha value cos4 deriving step comprises the steps of:
determining a value $TZEF2 = BU(K)*CU(L)*Z11 + BV(K)*CV(L)*Z22 + BW(K)*CW(L)*Z33 + (BV(K)*CW(L) + BW((K)*CV(L))*Z23 + (BU(K)*CW(L) + BW((K)*CU(L))*Z13 + (BU(K)*CV(L) + BV(K)*CU(L))*Z12$; and
deriving alpha value $cos4 = -TZEF2/(TZB(K)*TZC(L))$.

15. The method of claim 12 wherein said beta value cos5 deriving step comprises the steps of:
determining a value $TZEF3 = AU(J)*CU(L)*Z11 + AV(J)*CV(L)*Z22 + AW(J)*CW(L)*Z33 + (AV(J)*CW(L) + AW(J)*CV(L))*Z23 + (AU(J)*CW(L) + AW(J)*CU(L))*Z13 + (AU(J)*CV(L) + AV(J)*CU(L))*Z12$; and
deriving beta value $cos5 = TZEF3/(TZA(J)*TZC(L))$.

16. Automated apparatus for symmetry analysis of a crystalline material comprising:
a radiation generator for irridating a sample of the crystalline material with radiation;
a radiation detector for detecting radiation receiving from the irridated sample and producing electrical output signals indicative of the detected radiation;
a signal analyzer responsive to said electrical output signals produced by said radiation detector for producing edge data signals ZA, AB and ZC and angle data signals ZAL, ZBE and ZGA defining any primitive lattice cell Z of the material;
means for generating all symmetry matrices Hs which transform said cell Z into itself within predetermined maximum cell edge and angle parameter tolerances TOLI1, TOLI2, TOLI3 and TOLI4, TOLI5, TOLI6, respectively;
means for determining the metric symmetry using symmetry matrices Hs; and
means for determining the crystal symmetry using symmetry matrices Hs;

said symmetry matrix generating means being operative to find:
all matrix triples AU, AV, AW; BU, BV, BW; CU, CV, CW which accomplish transformation of the respective Z-cell edges to within the corresponding ones of said maximum cell edge tolerances; and
all combinations of said matrix triples which accomplish transformation of the respective Z-cell angles to within the corresponding ones of said maximum cell angle tolerances.

17. The apparatus of claim 16 wherein a diffractometer constitutes said radiation generator and radiation detector.

18. The apparatus of claim 17 wherein said diffractometer is selected from the group consisting of an x-ray diffractometer which irradiates the sample of the material with x-ray radiation, an electron diffractometer which irradiates the sample of the material with electron radiation, and a neutron diffractometer which irradiates the sample of the material with neutron radiation.

19. The apparatus of claim 17 wherein said signal analyzer further comprises a controller for controlling the orientation of the sample relative to said diffractometer.

20. The apparatus of claim 16 wherein an analytical electron microscope constitutes said radiation generator and radiation detector.

21. The apparatus of claim 16 wherein said symmetry matrix generating means operates to find matrix triples by:
defining a set of possible matrix H elements HEL(JJ), HEL(KK), HEL(LL), where JJ, KK, and LL range from one to a predetermined number NHEL;
determining dot products Z11, Z22, Z33, Z23, Z13 and Z12 for cell Z as follows:

$Z11 = ZA*ZA$ $Z22 = ZB*ZB$ $Z33 = ZC*ZC$ $Z23 = ZB*ZC*\cos(ZAL/RADIAN)$ $Z13 = ZA*ZC*\cos(ZBE/RADIAN)$ $Z12 = ZA*ZB*\cos(ZGA/RADIAN)$ $RADIAN = 360/2\pi;$ for each combination of HEL(JJ) HEL(KK) HEL(LL):
determining a symmetrical dot product TZEE for transformed cell Z, where $TZEE = HEL(JJ)*HEL(JJ)*Z11 + HEL(KK)*HEL(KK)*Z22 + HEL(LL)*HEL(LL)*Z33 + 2.0(HEL(KK)*\allowbreak *HEL(LL)*Z23 + HEL(JJ)*i \quad HEL(LL)*Z13 + HEL(JJ)*HEL(KK)*Z12)$;
determining whether TZEE is greater than zero, and if so, deriving a transformed Z-cell edge $TZEDG = \sqrt{TZEE}$; and
determining whether TZEDG is a transformation, within said respective tolerances TOLI1, TOLI2, and TOLI3, of any Z-cell edges ZA, AB, ZC; and if so, saving the HEL combination as a matrix triple AU, AV, AW; BU, BV, BW; and/or CU, CV, CW, and saving a value TZA, TZB and/or TZC = TZEDG, according to which edge(s) is (are) determined to be transformed.

22. The apparatus of claim 16 wherein said symmetry matrix generating means operates to find matrix triple combinations by:
for each pair of matrix triples AU, AV, AW and BU, BV, BW:
deriving a gamma value cos6 for a transformed cell TZ;
determining whether gamma value cos6 is greater than or equal to +1 or less than or equal to −1, and if not, converting gamma value cos6 to an angle value TZGA;
determining whether TZGA is within said maximum allowable tolerance TOLI6, and if so for each matrix triple CU, CV, CW:
deriving the determinant HDET of the transformation matrix defined by the combination of matrix triples AU, AV, AW; BU, BV, BW and CU, CV, CW;
determining whether HDET is equal to one, and if so, deriving an alpha value cos4 for said transformed cell TZ;
determining whether alpha value cos4 is greater than or equal to +1 or less than or equal to −1, and if not, converting alpha value cos4 to an angle value TZAL;
determining whether TZAL is within said maximum allowable tolerance TOLI4, and if so, deriving a beta value cos5 for said transformed cell TZ;
determining whether beta value cos5 is greater than or equal to +1 or less than or equal to −1, and if not, converting beta value cos5 to an angle value TZBE;
determining whether TZBE is within said maximum allowable tolerance TOLI4, and if so, saving the combination of matrix triples as the elements U1, V1, W1, U2, V2, W2, U3, V3 and W3 of a symmetry matrix Hs.

23. The apparatus of claim 22 wherein said gamma value cos6 is derived by:
determining a value $TZEF1 = AU(J)*BU(K)*Z11 + AV(J)*BV(K)*Z22 + AW(J)*BW(K)*Z33 + (AV(J)*BW(K) + AW(J)*BV(K))*Z23 + (AU(J)*BW(K) + AW(J)*BU(K))*Z13 + (AU(J)*BV(K) + AV(J)*BU(K))*Z12$; and
deriving gamma value $\cos 6 = TZEF1/(TZA(J)*TZB(K))$.

24. The apparatus of claim 22 wherein said alpha value cos4 is derived by:
determining a value $TZEF2 = BU(K)*CU(L)*Z11 + BV(K)*CV(L)*Z22 + BW(K)*CW(L)*Z33 + (BV(K)*CW(L) + BW(K)*CV(L))*Z23 + (BU(K)*CW(L) + BW(K)*CU(L))*Z13 + (BU(K)*CV(L) + BV(K)*CU(L))*Z12$; and
deriving alpha value $\cos 4 = TZEF2/(TZB(K)*TZC(L))$.

25. The apparatus of claim 22 wherein said beta value cos5 is derived by:
determining a value $TZEF3 = AU(J)*CU(L)*Z11 + AV(J)*CV(L)*Z22 + AW(J)*CW(L)*Z33 + (AV(J)*CW(L) + AW(J)*CV(L))*Z23 + (AU(J)*CW(L) + AW(J)*CU(L))*Z13 + (AU(J)*CV(L) + AV(J)*CU(L))*Z12$; and deriving beta value $\cos 5 = TZEF3/(-TZA(J)*TZC(L))$.

26. Automated apparatus for comparing two lattices of crystalline materials to determine whether they have a predetermined lattice structure relationship therebetween, the apparatus comprising:
   at least one radiation generator for irridating samples of the crystalline materials with radiation;
   at least one radiation detector for detecting radiation received from the irridated samples and producing electrical output signals indicative of the detected radiation;
   a signal analyzer responsive to said electrical output signals produced by said at lest one radiation detector for determining primitive lattice cells Y and Z, respectively, for the two materials, said cells Y and Z having three cell edges YA, YB, YC and ZA, AB and AC, respectively, and three cell angles YAL, YBE, YGA and ZAL, ZBE and ZGA, respectively;
   means for generating all matrices H, if any, which transform cell Z into cell Y within predetermined maximum cell edge and angle tolerances TOLI1, TOLI2, TOLI3 and TOLI4, TOLI5, TOLI6, respectively; and
   means for determining whether any matrices H:
   1) have integer matrix elements and a determinant HDET=1, thereby determining that the two materials have the same lattice structure; or
   2) either a) have integer matrix elements, a determinant HDET>1, and will transform cell Z to cell Y; or b) have an inverse matrix H' which has integer elements, a determinant HDET 1, and will transform cell Y to cell Z, thereby determining that the two materials have lattice structures which are in a derivative subcell or supercell relationship; or
   3) both a) have at least one fractional matrix element and will transform cell Z to cell Y; and b) and an inverse matrix H' which also has at least one fractional matrix element and will transform cell Y to cell Z, thereby determining that the two materials have lattice structures which have a composite relationship.

27. The apparatus of claim 26 wherein at lest one diffractometer constitutes said at least one radiation generator and radiation detector.

28. The apparatus of claim 27 wherein said at least one diffractometer is selected from the group consisting of an x-ray diffractometer which irradiates a material sample with x-ray radiation, an electron diffractometer which irradiates a material sample with electron radiation, and a neutron diffractometer which irradiates a material sample with neutron radiation.

29. The apparatus of claim 27 wherein said signal analyzer further comprises a controller for controlling the orientation of the samples relative to said at least one diffractometer.

30. The apparatus of claim 26 wherein at lest one analytical electron microscope constitutes said at least one radiation generator and radiation detector.

31. The apparatus of claim 26 wherein said means for generating matrices H operates by:
   finding all matrix triples AU, AV, AW; BU, BV, BW; CU, CV, CW which accomplish transformation of the respective Z-cell edges to the corresponding Y-cell edges within said maximum cell edge tolerances;
   finding all combinations of said matrix triples found in said matrix triple finding step which accomplish transformation of the respective Z-cell angles to the corresponding Y-cell angles within said maximum cell angle tolerances.

32. The apparatus of claim 31 wherein matrix triples are found by:
   defining a set of possible matrix H elements HEL(JJ), HEL(KK), HEL(LL), where JJ, KK, and LL range from one to a predetermined number NHEL;
   determining dot products Z11, Z22, Z33, Z23, Z13 and Z12 for cell Z as follows:

$Z11 = ZA*ZA$ $Z22 = ZB*ZB$ $Z33 = ZC*ZC$ $Z23 = ZB*ZC*\cos(ZAL/RADIAN)$ $Z13 = ZA*ZA*\cos(ZBE/RADIAN)$ $Z12 = ZA*ZB*\cos(ZGA/RADIAN)$ $RADIAN = 360/2\pi$;

for each combination of HEL(JJ) HEL(KK) HEL(LL):
   determining a symmetrical dot product TZEE for transformed cell Z, where $TZEE = HEL(JJ)*HEL(JJ)*Z11 + HEL(KK)*HEL(KK)*Z22 + HEL(LL)*HEL(LL)*Z33 + 2.0(HEL(KK)*HEL(LL)*Z23 + HEL(JJ)8HEL(LL)*Z13 + HEL(JJ)*HEL(KK)*Z12)$;
   determining whether TZEE is greater than zero, and if so, deriving a transformed Z-cell edge $TZEG = \sqrt{TZEE}$; and
   determining whether TZEDG is a transformation, within said respective tolerances TOLI1, TOLI2, and TOLI3, of any of Z-cell edges ZA, ZB, ZC, to a corresponding one of the Y-cell edges YA, YB, YC; and if so, saving the HEL combination as a matrix triple AU, AV, AW; BU, BV, BW; or CU, CV, CW, and saving a value TZA, TAB, and/or TZC=TZEDG, according to which edge(s) is (are) determined to be transformed.

33. The apparatus of claim 31 wherein matrix triple combinations are found by:
   for each pair of matrix triples AU, AV, AW and BU, BV, BW:
   deriving a gamma value cos6 for a transformed cell TZ;
   determining whether gamma value cos6 is greater than or equal to +1 or less than or equal to −1, and if not, converting gamma value cos6 to an angle value TZGA;
   determining whether TZGA is within said maximum allowable tolerance TOLI6, and if so, for each matrix triple CU, CV, CW:
   deriving the determinant HDET of the transformation matrix defined by the combination of matrix triples AU, AV, AW; BU, BV, BW and CU, CV, CW;
   determining whether HDET is greater than zero, and if so, deriving an alpha value cos4 for said transformed cell TZ;
   determining whether alpha value cos4 is greater than or equal to +1 or less than or equal to −1, and if not, converting alpha value cos4 to an angle value TZAL;

determining whether TZAL is within said maximum allowable tolerance TOLI4, and if so, deriving a beta value cos5 for said transformed cell TZ;

determining whether beta value cos5 is greater than or equal to $+1$ or less than or equal to $-1$, and if not, converting beta value cos5 to an angle value TZBE;

determining whether TZBE is within said maximum allowable tolerance TOLI4, and if so, saving the combination of matrix triples as the elements U1, V1, W1, U2, V2, W2, U3, V3 and W3 of a transformation matrix H.

34. The apparatus of claim 31 wherein said gamma value cos6 is derived by:

determining a value $TZEF1 = AU(J)*BU(K)*Z11 + AV(J)*BV(K)*Z22 + AW(J)*BW(K)*Z33 + (AV(J)*BW(K)) + AW(J)*BV(K))*Z23 + (AU(J)*BW(K) + AW(K)*BU(K))*Z13 + (AU(J)*BV(K) + AV(J)*BU(-K))*Z12$; and deriving gamma value $cos6 = TZEF1/(TZA(J)*TZB(K))$.

35. The apparatus of claim 31 wherein said alpha value cos4 is derived by:

determining a value $TZEF2 = BU(K)*CU(L)*Z11 + BV(K)*CV(L)*Z22 + BW(K)*CW(L)*Z33 + (BV(K)*CW(L) + BW(K)*-CV(L))*Z23 + (BU(K)*CW(L) + BW(K)*CU(L))*Z13 + (BU(K)*CV(L) + BV(K)*CU(L))*Z12$; and deriving alpha value $cos4 = TZEF2/(TZB(K)*TZC(L))$.

36. The apparatus of claim 31 wherein said beta value cos5 is derived by:

determining a value $TZEF3 = AU(J)*CU(L)*Z11 + AV(J)*CV(L)*Z22 + AW(J)*CW(L)*Z33 + (AV(J)*CW(L) + AW(J)*-CV(L))*Z23 + (AU(J)*CW(L) + AW(J)*CU(L))*Z13 + (AU(J)*CV(L) + AV(J)*CU(L))*Z12$; and deriving beta value $cos5 = TZEF3/(TZA(J)*TZC(L))$.

37. Automatic apparatus for identifying an unknown crystalline material comprising:

an electronic signal analyzer, responsive to electrical signals generated by detecting radiation received from a sample of the unknown material which has been irradiated by radiation, for producing electrical data signal outputs indicative of a primitive lattice cell Z of the unknown material, said cell Z having three cell edges ZA, ZB and ZC, respectively, and three cell angles ZAL, ZBE, and ZGA, respectively;

a first computer accessible memory in which is stored a database for materials with known lattice structures and chemical compositions, said database comprising lattice cell data and element type data identifying the lattice structures and chemical compositions, respectively, of the database materials;

first computer search means responsive to said electronic signal analyzer data signal outputs for automatically searching said database using a converse transformation method to generate matrices H identifying all materials, if any, having lattice cell structures related to cell Z;

computer means for analyzing any matrices H generated by said first search means to identify which of the database materials identified by the generated matrices H match cell Z by having a lattice cell structure identical to or in a subcell/supercell derivative relationship to cell Z, any database material so identified as matching cell Z constituting a possible identification of the unknown crystalline material;

means for determining the element types identifying the chemical composition of the unknown material and producing electrical signal outputs indicative of the unknown material element types;

second computer search means responsive to the electrical signal outputs produced by said element type determining means for automatically searching said database for all compounds which match the unknown material by having the same or related element types as the unknown material;

a computer accessible second memory for saving as a first data set the compounds matching cell Z identified by said matrix H analyzing means, and as a second data set the matching compounds with the same element types as the unknown material identified by said second search means; and said computer means includes means for combining said first and second data sets stored in said electronic memory to derive all known compounds having the same lattice cell structure and element types as the unknown material.

* * * * *